US009932377B2

(12) United States Patent
Keefe et al.

(10) Patent No.: US 9,932,377 B2
(45) Date of Patent: Apr. 3, 2018

(54) MITOCHONDRIAL TARGETING AND THERAPEUTIC USE THEREOF

(71) Applicant: Shire Human Genetic Therapies, Inc., Lexington, MA (US)

(72) Inventors: Dennis Keefe, Wilmington, MA (US); Michael Concino, Bolton, MA (US); Michael Heartlein, Boxborough, MA (US); Serene Josiah, Cambridge, MA (US); Bettina Strack-Logue, Somerville, MA (US)

(73) Assignee: Shire Human Genetic Therapies, Inc., Lexington, MA (US)

( * ) Notice: Subject to any disclaimer, the term of this patent is extended or adjusted under 35 U.S.C. 154(b) by 138 days.

(21) Appl. No.: 14/993,500

(22) Filed: Jan. 12, 2016

(65) Prior Publication Data

US 2016/0237129 A1 Aug. 18, 2016

Related U.S. Application Data

(62) Division of application No. 14/127,074, filed as application No. PCT/US2012/042779 on Jun. 15, 2012, now Pat. No. 9,260,495.

(60) Provisional application No. 61/498,430, filed on Jun. 17, 2011.

(51) Int. Cl.
| | | |
|---|---|---|
| *C07K 14/47* | (2006.01) | |
| *A61K 38/17* | (2006.01) | |
| *A61K 49/00* | (2006.01) | |
| *C07K 7/08* | (2006.01) | |
| *A61K 47/64* | (2017.01) | |
| *A61K 38/00* | (2006.01) | |

(52) U.S. Cl.
CPC .......... *C07K 14/47* (2013.01); *A61K 38/1709* (2013.01); *A61K 47/645* (2017.08); *A61K 49/0008* (2013.01); *C07K 7/08* (2013.01); *A01K 2217/075* (2013.01); *A01K 2227/105* (2013.01); *A01K 2267/0306* (2013.01); *A61K 38/00* (2013.01); *C07K 2319/07* (2013.01); *C07K 2319/10* (2013.01)

(58) Field of Classification Search
CPC ..................................................... C07K 14/47
See application file for complete search history.

(56) References Cited

U.S. PATENT DOCUMENTS

| | | |
|---|---|---|
| 2003/0190364 A1 | 10/2003 | Panitch et al. |
| 2004/0101874 A1 | 5/2004 | Ghosh et al. |
| 2005/0169904 A1 | 8/2005 | Payne |
| 2007/0059710 A1 | 3/2007 | Luke et al. |

FOREIGN PATENT DOCUMENTS

| | | |
|---|---|---|
| WO | WO-2005/042560 A2 | 5/2005 |
| WO | WO-2009/098682 A2 | 8/2009 |
| WO | WO-2009/099679 A2 | 8/2009 |

OTHER PUBLICATIONS

American Heart Association, BCVS Conference 2008 Abstracts, Circulation Research, 103(5): e35-e70 (2008).
Campuzano et al., Frataxin is Reduced in Friedreich Ataxia Patients and is Associated with Mitochondrial Membranes., Hum. Mol. Genet. (1997), vol. 6(11 ), pp. 1771-1780.
Gakh, O. et al., Physical evidence that yeast frataxin is an iron storage protein, Biochemistry, 41: 6798-6804 (2002).
Guo, H., et al., Protein tolerance to random amino acid change, 2004, Proc. Natl. Acad. Sci. USA 101: 9205-9210.
Hill, M., et al., Functional Analysis of Conserved Histidines in ADP-Glucose Pyrophosphorylase from *Escherichia coli*, 1998, Biochem. Biophys. Res. Comm. 244:573-577.
International Preliminary Report on Patentability for PCT/US12/42779, dated Jan. 3, 2014, published as WO 2012/174452 (9 pages).
Kim, M.J. et al., Protective effects of transduced PEP-1-Frataxin protein on oxidative stress-induced neuronal cell death, Journal of Neurological Sciences, 298(1-2): 64-69 (2010).
Koczor, C., A., et al., Mitochondrial DNA damage initiates a cell cycle arrest by a Chk2-associated mechanism in mammalian cells., The Journal of Biological Chemistry (2009), vol. 284(52), pp. 36191-36201.
Lazar, E., et al., Transforming Growth Factor a: Mutation of Aspartic Acid 4 7 and Leucine 48 Results in Different Biological Activity, 1988, Mol. Cell. Biol. 8:1247-1252.
Pandolfo and Pastore, The pathogenesis of Friedreich ataxia and the structure and function of frataxin, J. Neurol., 256(Suppl. 1): 9-17 (2009).
Pastore, A. and Puccio, H., Frataxin: a protein in search for a function, Journal of Neurochemistry, 126(Suppl. 1): 43-52 (2013).
Patel, P.I. and Isaya, G., Friedreich ataxia: from GAA triplet-repeat expansion to frataxin deficiency, Am. J. Hum. Genet. 69:15-24 (2001).
Schmucker, S. and Puccio, H., Understanding the molecular mechanisms of Friedreich's ataxia to develop therapeutic approaches, Human Molecular Genetics, 19(R1): R103-110 (2010).
Schmucker, S., et al., The in vivo mitochondrial two-step maturation of human frataxin, Human Molecular Genetics, (2008), vol. 17, No. 22, 3521-3531.

(Continued)

*Primary Examiner* — Maryam Monshipouri
(74) *Attorney, Agent, or Firm* — Fangli Chen; Proskauer Rose LLP

(57) ABSTRACT

The present invention provides, among other things, compositions and methods for treatment of Friedrich's Ataxia based on effective targeting of a therapeutic moiety to mitochondria that can substitute for natural FXN protein activity or rescue one or more phenotypes or symptoms associated with frataxin-deficiency. In some embodiments, the present invention provides a targeted therapeutic comprising a therapeutic moiety, which is a polypeptide having an N-terminus and a C-terminus, a mitochondrial targeting sequence associated with the therapeutic moiety at the N-terminus, and a mitochondrial membrane-penetrating peptide associated with the therapeutic moiety at the C-terminus, wherein the therapeutic moiety is targeted to mitochondria upon cellular entry.

4 Claims, 10 Drawing Sheets

(56) References Cited

OTHER PUBLICATIONS

Supplementary European Search Report for EP12801238, 9 pages (dated Oct. 23, 2014).
UNIPROT. FRDA-Human 5, Retrieved Aug. 24, 2012 from the internet: <URL: http://www.uniprot.org/uniprot/Q16595.txt?version=122>, especially p. 1, 8 and 9 (Apr. 5, 2011).
Wacey et al., Disentangling the perturbational effects of amino acid substitutions in the DNA-binding domain of p53., Hum Genet, 1999, vol. 104, pp. 15-22.
Written Opinion for PCT/US12/42779, 10 pages (dated Sep. 7, 2012).

C TERMINAL TAT
*MGHHHHHH*GSLQEEKPKEGVKTENDHINLKVAGQDGSVVQFKIKRHTPLSKLMKAYCER
QGLSMRQIRFRFDGQPINETDTPAQLEMEDEDTIDVFQQQTGGMWTLGRRAVAGLLASPS
PAQAQTLTRVPRPAELAPLCGRRGLRTDIDATCTPRRASSNQRGLNQIWNVKKQSVYLM
NLRKSGTLGHPGSLDETTYERLAEETLDSLAEFFEDLADKPYTFEDYDVSFGSGVLTVKLG
GDLGTYVINKQTPNKQIWLSSPSSGPKRYDWTGKNWVYSHDGVSLHELLAAELTKALKTK
LDLSSLAYSGKDA*GYGRKKRRQRRR*

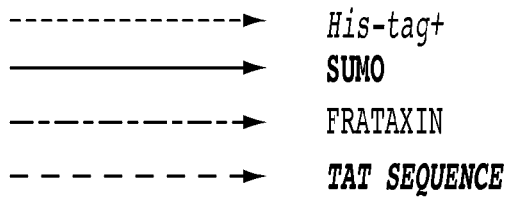

*His-tag+*
SUMO
FRATAXIN
*TAT SEQUENCE*

N TERMINAL TAT
*MGHHHHHH*GSLQEEKPKEGVKTENDHINLKVAGQDGSVVQFKIKRHTPLSKLMKAYCER
QGLSMRQIRFRFDGQPINETDTPAQLEMEDEDTIDVFQQQTGG*GYGRKKRRQRRR*MWTL
GRRAVAGLLASPSPAQAQTLTRVPRPAELAPLCGRRGLRTDIDATCTPRRASSNQRGLN
QIWNVKKQSVYLMNLRKSGTLGHPGSLDETTYERLAEETLDSLAEFFEDLADKPYTFEDY
DVSFGSGVLTVKLGGDLGTYVINKQTPNKQIWLSSPSSGPKRYDWTGKNWVYSHDGVSL
HELLAAELTKALKTKLDLSSLAYSGKDA

FIG. 1

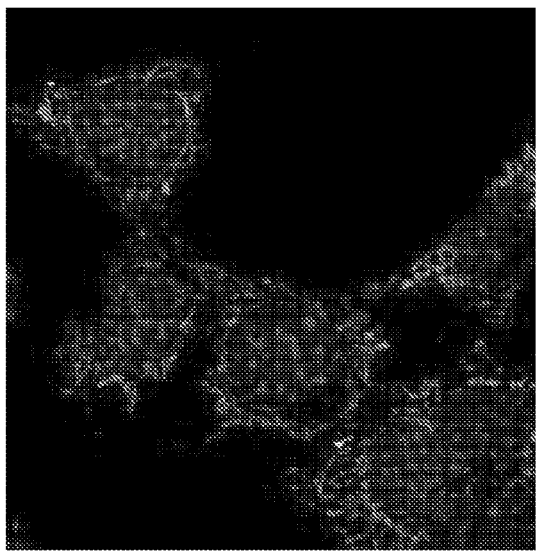 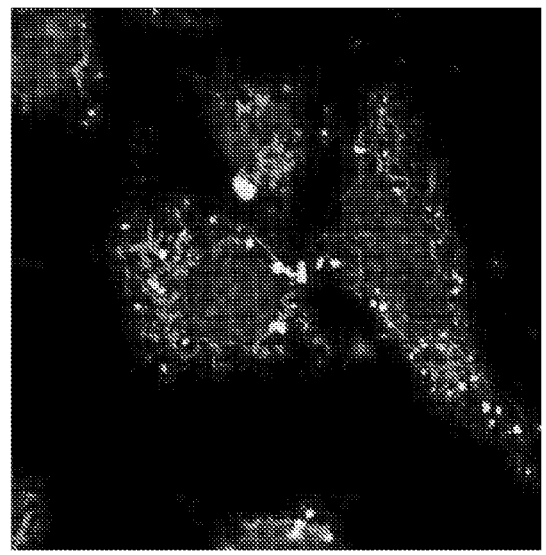
FIG. 5

MITOCHONDRIAL TARGETING AND THERAPEUTIC USE THEREOF

CROSS REFERENCE TO RELATED APPLICATIONS

This application is a divisional of U.S. patent application Ser. No. 14/127,074, a National Stage Application filed under 35 U.S.C. § 371 based on International Application No. PCT/US2012/42779, filed Jun. 15, 2012 which claims priority to U.S. provisional patent application Ser. No. 61/498,430, filed Jun. 17, 2011. The disclosures of each of which are hereby incorporated in their entirety.

SEQUENCE LISTING

In accordance with 37 C.F.R. § 1.52(e)(5), the present specification makes reference to a Sequence Listing (submitted electronically as a .txt file named "SHR-1057US2DIV_SequenceListing".txt, on Apr. 29, 2016) The .txt file was generated on Apr. 28, 2016 and is 8,646 bytes in size. The entire contents of the Sequence Listing are incorporated herein by reference.

BACKGROUND

Friedreich's Ataxia (FRDA) is a rare but serious degenerative neuromuscular disease resulting from diminished levels of the mitochondrial protein Frataxin (FXN) (reviewed by Schmucker and Puccio, *Human Molecular Genetics*, 2010 Apr. 15; 19(R1): R103-110; Pandolfo and Pastore, *J. Neurol*, 2009, 256 (Suppl. 1), 9-17). The function of FXN is not entirely clear, but it seems to be involved in assembly of iron-sulfur clusters. It has been proposed to act as either an iron chaperone or an iron storage protein. In many cases, FRDA is caused by a large expansion of a GAA triplet-repeat sequence in the first intron of the frataxin gene, which can lead to decreased transcription of full-length transcripts (P. Patel and G. Isaya, Am. J. Hum. Genet. 69:15-24 (2001)). As a result, FRDA patients suffer progressive iron accumulation and dysfunction in mitochondria (O. Gakh, et al., *Biochemistry*, 41:6798-6804 (2002)), resulting in symptoms that may include mild to severe muscular impairments, including ataxia, fatigue, muscle loss, blurring of vision, and slurring of speech. In addition, FRDA patients may develop severe and life threatening cardiomyopathies and are susceptible to motorneuron dysfunction and FRDA-associated diabetes mellitus. Symptoms typically begin sometime between the ages of 5 to 15 years, but in Late Onset, FRDA may occur in the 20s or 30s. Patients with FRDA typically die by the 4$^{th}$ or 5$^{th}$ decade of life.

Currently, there is no approved therapy for treatment of FRDA.

SUMMARY OF THE INVENTION

The present invention provides compositions and methods for effective treatment of Friedreich's Ataxia (FRDA) based on Frataxin (FXN) protein replacement therapy. The present invention is, in part, based on the discovery that the presence of a mitochondrial membrane-penetrating peptide at the C-terminus of a recombinant FXN is unexpectedly effective in targeting the FXN protein to mitochondria, in particular, in cellular targets underlying FRDA pathophysiology such as cardiomyocytes and neurons of the dorsal root ganglia, and rescuing FXN-deficient cells from cell death.

Thus, in one aspect, the present invention provides targeted therapeutics including a therapeutic moiety, which is a polypeptide having an N-terminus and a C-terminus and an amino acid sequence at least 70% (e.g., at least 75%, 80%, 85%, 90%, 95%, or 98%) identical to mature human Frataxin protein (SEQ ID NO:1); a mitochondrial targeting sequence; and a mitochondrial membrane-penetrating peptide, wherein the mitochondrial targeting sequence is associated with the N-terminus of the therapeutic moiety and the mitochondrial membrane-penetrating peptide is associated with the C-terminus of the therapeutic moiety, and further wherein the therapeutic moiety is targeted to mitochondrial upon cellular entry.

In some embodiments, the mitochondrial targeting sequence and the mitochondrial membrane-penetrating peptide are conjugated to the therapeutic moiety. In some embodiments, the mitochondrial targeting sequence and the mitochondrial membrane-penetrating peptide are fused to the therapeutic moiety in a fusion protein configuration. In some embodiments, the mitochondrial targeting sequence or the mitochondrial membrane-penetrating peptide is fused to the therapeutic moiety via a linker.

In certain embodiments, the mitochondrial targeting sequence has an amino acid sequence at least 70% (e.g., at least 75%, 80%, 85%, 90%, 95%, or 98%) identical to SEQ ID NO:2. In some embodiments, the mitochondrial membrane-penetrating peptide has an amino acid sequence at least 80% identical to HIV-TAT peptide GYGRKKRRQRRR (SEQ ID NO:5).

In another aspect, the present invention provides targeted therapeutics including a therapeutic moiety, which is a polypeptide having an N-terminus and C-terminus and an amino acid sequence at least 70% (e.g., at least 75%, 80%, 85%, 90%, 95%, or 98%) identical to full-length human Frataxin protein (SEQ ID NO:4); and a mitochondrial membrane-penetrating peptide, wherein the mitochondrial membrane-penetrating peptide is associated with the C-terminus of the therapeutic moiety, and further wherein the therapeutic moiety is targeted to mitochondria upon cellular entry.

In some embodiments, the mitochondrial membrane-penetrating peptide contains at least three (e.g., at least four, five, six, seven, eight, nine, ten, or eleven) contiguous amino acids that appear in the HIV-TAT peptide GYGRKKRRQRRR (SEQ ID NO:5). In some embodiments, the at least three (e.g., at least four, five, six, seven, eight, nine, ten, or eleven) contiguous amino acids maintain their relative positions as they appear in SEQ ID NO:5. In some embodiments, the mitochondrial membrane-penetrating peptide has an amino acid sequence at least 70% (e.g., at least 75%, 80%, 85%, 90%, or 95%) identical to SEQ ID NO:5. In some embodiments, the mitochondrial membrane-penetrating peptide comprises amino acid sequence GYGRKKRRQRRR (SEQ ID NO:5).

In certain embodiments, the therapeutic moiety comprises an amino acid sequence at least 70% (e.g., at least 75%, 80%, 85%, 90%, 95%, or 98%) identical to full-length human Frataxin protein (SEQ ID NO:4). In some embodiments, the therapeutic moiety comprises a full length human Frataxin protein (SEQ ID NO:4).

In some embodiments, the mitochondrial membrane-penetrating peptide is conjugated to the C-terminus of the therapeutic moiety. In some embodiments, the mitochondrial membrane-penetrating peptide is fused to the C-terminus of the therapeutic moiety in a fusion protein configuration. In some embodiments, the mitochondrial membrane-penetrating peptide is fused to the C-terminus of the therapeutic moiety via a linker.

In yet another aspect, the present invention provides targeted therapeutic fusion proteins comprising an amino acid sequence at least 70% (e.g., at least 75%, 80%, 85%, 90%, 95%, or 98%) identical to SEQ ID NO:6. In some embodiments, the amino acid sequence is at least 80% identical to SEQ ID NO:6. In some embodiments, the amino acid sequence is at least 85% identical to SEQ ID NO:6. In some embodiments, the amino acid sequence is at least 90% identical to SEQ ID NO:6. In some embodiments, the amino acid sequence is at least 95% identical to SEQ ID NO:6. In some embodiments, the amino acid sequence is identical to SEQ ID NO:6.

Among other things, the present invention provides nucleic acids encoding various targeted therapeutic fusion proteins described herein and cells comprising a nucleic acid according to the invention. In addition, the present invention provides methods for producing a targeted therapeutic fusion protein by culturing the cells described herein under conditions permitting expression of the therapeutic fusion protein.

In still another aspect, the present invention provides methods of targeting a therapeutic moiety to mitochondria, including contacting a cell with a targeted therapeutic comprising a therapeutic moiety, which is a polypeptide having an N-terminus and a C-terminus, and associated with a mitochondrial targeting sequence at the N-terminus and a mitochondrial membrane-penetrating peptide at the C-terminus; and wherein the therapeutic moiety traffics to mitochondria upon cellular entry. In some embodiments, the therapeutic moiety has an amino acid sequence at least 70% (e.g., at least 75%, 80%, 85%, 90%, 95%, or 98%) identical to mature human Frataxin protein (SEQ ID NO:1). In some embodiments, the mitochondrial targeting sequence has an amino acid sequence at least 70% (e.g., at least 75%, 80%, 85%, 90%, 95%, or 98%) identical to SEQ ID NO:2. In some embodiments, the mitochondrial membrane-penetrating peptide has an amino acid sequence at least 80% identical to HIV-TAT peptide GYGRKKRRQRRR (SEQ ID NO:5).

In some embodiments, the cell is deficient in Frataxin. In some embodiments, the cell is a cultured cell. In some embodiments, the cell is selected from fibroblasts, primary cardiomyocytes, and/or primary neurons of the dorsal root ganglia (DRG). In some embodiments, the cell is an in vivo cellular target.

In some embodiments, targeting the therapeutic moiety to mitochondria improves cell survival caused by Frataxin deficiency.

In a further aspect, the present invention provides methods of treating Friedreich's Ataxia including administering to a subject in need of treatment a targeted therapeutic described herein. In some embodiments, a method according to the invention comprises a therapeutic moiety, which is a polypeptide having an N-terminus and a C-terminus and having an amino acid sequence at least 70% (e.g., at least 75%, 80%, 85%, 90%, 95%, or 98%) identical to mature human frataxin protein (SEQ ID NO:1); wherein the therapeutic moiety is associated with a mitochondrial targeting sequence at the N-terminus and a mitochondrial membrane-penetrating peptide at the C-terminus.

As used in this application, the terms "about" and "approximately" are used as equivalents. Any numerals used in this application with or without about/approximately are meant to cover any normal fluctuations appreciated by one of ordinary skill in the relevant art.

Other features, objects, and advantages of the present invention are apparent in the detailed description that follows. It should be understood, however, that the detailed description, while indicating embodiments of the present invention, is given by way of illustration only, not limitation. Various changes and modifications within the scope of the invention will become apparent to those skilled in the art from the detailed description.

BRIEF DESCRIPTION OF THE DRAWINGS

The drawings are for illustration purposes only, not for limitation.

FIG. 1 depicts amino acid sequences of exemplary C- and N-terminal FXN-TAT fusion proteins (SEQ ID NO:6 and SEQ ID NO:7, respectively).

FIG. 5 depicts exemplary results illustrating localization of N-terminal FXN-TAT fusion proteins in mouse fibroblasts in the presence of chloroquine following exogenous addition of protein directly to cell culture media. NC6 SV40 mouse fibroblasts were plated overnight on collagen coated cover-slips. The following day, N-terminal FXN-TAT was added directly to cell culture media at a final concentration of 2.5 µM, in the presence or absence of 25 µM chloroquine. Cells were treated with protein for four hours, following which they were trypsinized to remove non-incorporated protein and replated onto collagen coated cover-slips, in the presence or absence of chloroquine. Cells were allowed to adhere overnight. The following day, cells were treated with 200 nM Mitotracker Red CMX Rosamine for thirty minutes to stain mitochondria, then fixed and processed for anti-frataxin immunofluorescent staining using monoclonal antibody 18A5DB1 (from Mitosciences, specific for human frataxin). In the absence of chloroquine, FXN-TAT is degraded within the cell cytoplasm, while in the presence of chloroquine, FXN-TAT staining is apparent throughout the cytoplasm in a vesicular, non-mitochondrial pattern.

DEFINITIONS

Figure 2:
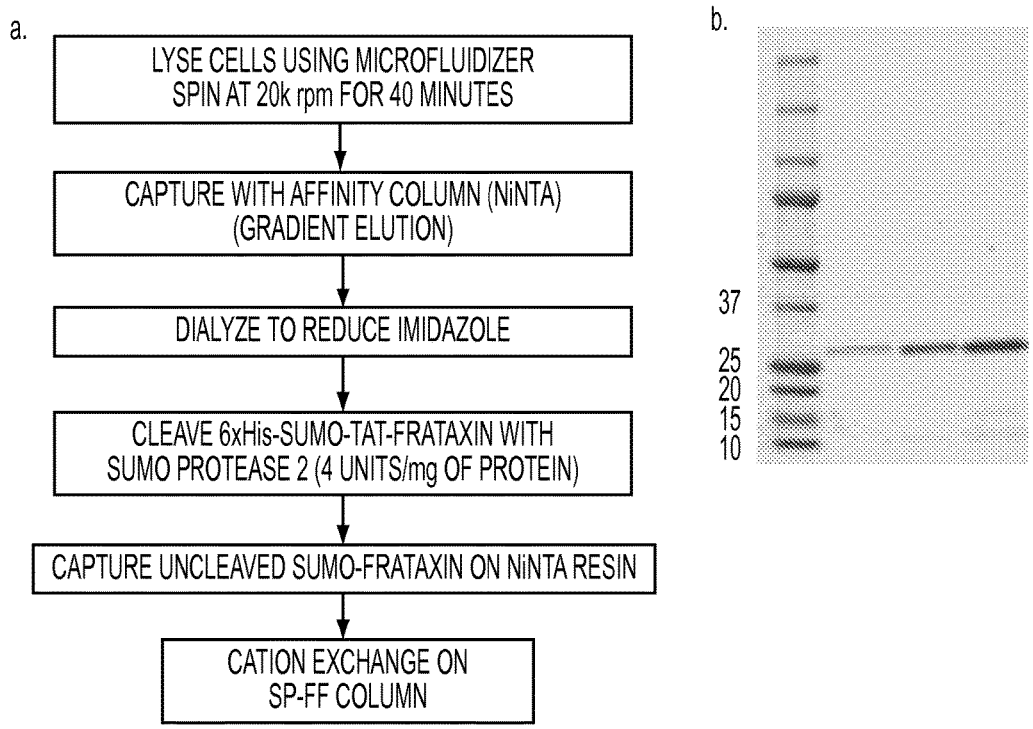
FIG. 2 depicts an exemplary purification process of C- and N-terminal FXN-TAT fusion proteins. (A) Depicts a summary of an exemplary purification scheme; (B) Depicts an exemplary SDS-PAGE analysis of a representative batch of C terminal FXN-TAT. Increasing amounts of recombinant C terminal FXN-TAT protein (2, 5 and 10 µg) were added in each lane. Recombinant FXN-TAT fusion proteins were routinely >95% pure by SDS-PAGE and rp-HPLC analysis.

In order for the present invention to be more readily understood, certain terms are first defined below. Additional definitions for the following terms and other terms are set forth throughout the specification.

Amelioration: As used herein, the term "amelioration" is meant the prevention, reduction or palliation of a state, or improvement of the state of a subject. Amelioration includes, but does not require complete recovery or complete prevention of a disease condition (e.g., FRDA). In some embodiments, amelioration includes increasing levels of relevant protein or its activity (e.g., FXN) that is deficient in relevant disease tissues.

Biologically active: As used herein, the phrase "biologically active" refers to a characteristic of any agent that has activity in a biological system, and particularly in an organism. For instance, an agent that, when administered to an organism, has a biological effect on that organism, is considered to be biologically active. In particular embodiments, where a protein or polypeptide is biologically active, a portion of that protein or polypeptide that shares at least one biological activity of the protein or polypeptide is typically referred to as a "biologically active" portion.

Improve, increase, or reduce: As used herein, the terms "improve," "increase" or "reduce," or grammatical equivalents, indicate values that are relative to a baseline measurement, such as a measurement in the same individual prior to initiation of the treatment described herein, or a measurement in a control individual (or multiple control individuals) in the absence of the treatment described herein. A "control individual" is an individual afflicted with the same form of degenerative disease (e.g., FRDA) as the individual being treated, who is about the same age as the individual being treated (to ensure that the stages of the disease in the treated individual and the control individual(s) are comparable).

Individual, subject, patient: As used herein, the terms "subject," "individual" or "patient" refer to a human or a non-human mammalian subject. The individual (also referred to as "patient" or "subject") being treated is an individual (fetus, infant, child, adolescent, or adult human) suffering from a disease, for example, Friedreich's Ataxia (FRDA).

Linker: As used herein, the term "linker" refers to, in a fusion protein, an amino acid sequence other than that appearing at a particular position in the natural protein and is generally designed to be flexible or to interpose a structure, such as an a-helix, between two protein moieties. For example, in some embodiments, a mitochondrial targeting sequence and/or a mitochondrial membrane-penetrating peptide may be associated with a FXN protein via a linker. A linker is also referred to as a spacer.

Mitochondrial Protein: As used herein, the term "mitochondrial protein" refers to any protein (e.g., FXN) that is capable of localizing to the mitochondrion of a cell. In some embodiments, a mitochondrial protein (e.g., FXN) is capable of improving symptoms related to a degenerative disorder associated with diminished levels of protein in the mitochondria (e.g., Friedreich's Ataxia), such as ataxia, fatigue, muscle loss, blurring of vision, slurring of speech, cardiomyopathy, and diabetes mellitus. Mitochondrial proteins suitable for the invention include both wild-type or modified mitochondrial proteins and can be produced using recombinant and synthetic methods or purified from natural sources. For example, mitochondrial proteins used herein encompass any proteins or protein conjugates that are capable of substituting for a naturally-occurring mitochondrial protein.

Mitochondrial membrane-penetrating peptide: As used herein, the term "mitochondrial membrane-penetrating peptide" refers to any peptide that is capable of directing a protein to penetrate the mitochondrial membrane within a cell. Exemplary mitochondrial membrane penetrating peptides include, but are not limited to, HIV-TAT, Antp, penetratin, polylysine, polyarginie, VP22, Syn B1, PTD-4, Pep-1, transportan and FGF-4 peptides. Suitable mitochondrial membrane penetrating peptides can be produced using recombinant and synthetic methods or purified from natural sources and encompass both naturally-occurring sequences and modified sequences that retain mitochondrial penetrating ability. In many embodiments, mitochondrial membrane penetrating peptides are also capable of penetrating cell membrane. Such mitochondrial membrane penetrating peptides are particularly useful for the present invention. Thus, in some embodiments, the terms "mitochondrial membrane penetrating peptides" and "cell penetrating peptides" are used interchangeably.

Mitochondrial targeting sequence: As used herein, the term "mitochondrial targeting sequence" refers to any peptide that is capable of directing a protein to the mitochondrion of a cell. Many mitochondrial proteins contain an intrinsic mitochondrial targeting sequence, typically, at the N-terminus. For example, the full-length frataxin protein contains a mitochondrial targeting sequence at the N-terminus (e.g., the N-terminal 20 amino acids). Additional examples of mitochondrial targeting sequences include, but are not limited to, amphiphilic helices of high arginine or lysine content, such as the sequences found in the cytochrome C oxidase subunit IV (Cox IV) and ornithine transcarbylamse (OTC) proteins. Suitable mitochondrial targeting sequences can be produced using recombinant and synthetic methods or purified from natural sources and encompass both naturally-occurring sequences and modified sequences that retain mitochondrial targeting ability.

Polypeptide: As used herein, a "polypeptide", generally speaking, is a string of at least two amino acids attached to one another by a peptide bond. In some embodiments, a polypeptide may include at least 3-5 amino acids, each of which is attached to others by way of at least one peptide bond. Those of ordinary skill in the art will appreciate that polypeptides sometimes include "non-natural" amino acids or other entities that nonetheless are capable of integrating into a polypeptide chain, optionally.

Substantial homology: The phrase "substantial homology" is used herein to refer to a comparison between amino acid or nucleic acid sequences. As will be appreciated by those of ordinary skill in the art, two sequences are generally considered to be "substantially homologous" if they contain homologous residues in corresponding positions. Homologous residues may be identical residues. Alternatively, homologous residues may be non-identical residues will appropriately similar structural and/or functional characteristics. For example, as is well known by those of ordinary skill in the art, certain amino acids are typically classified as "hydrophobic" or "hydrophilic" amino acids, and/or as having "polar" or "non-polar" side chains Substitution of one amino acid for another of the same type may often be considered a "homologous" substitution.

As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul, et al., Basic local alignment search tool, *J. Mol. Biol.*, 215(3): 403-410, 1990; Altschul, et al., *Methods in Enzymology*; Altschul, et al., "Gapped BLAST and PSI-BLAST: a new generation of protein database search programs", *Nucleic Acids Res.* 25:3389-3402, 1997; Baxevanis, et al., *Bioinformatics A Practical Guide to the Analysis of Genes and Proteins*, Wiley, 1998; and Misener, et al., (eds.), *Bioinformatics Methods and Protocols* (Methods in Molecular Biology, Vol. 132), Humana Press, 1999. In addition to identifying homologous sequences, the programs mentioned above typically provide an indication of the degree of homology. In some embodiments, two sequences are considered to be substantially homologous if at least 50%, 55%, 60%, 65%, 70%, 75%, 80%, 85%, 90%, 91%, 92%, 93%, 94%, 95%, 96%, 97%, 98%, 99% or more of their corresponding residues are homologous over a relevant stretch of residues. In some embodiments, the relevant stretch is a complete sequence. In some embodiments, the relevant stretch is at least 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500 or more residues.

Substantial identity: The phrase "substantial identity" is used herein to refer to a comparison between amino acid or nucleic acid sequences. As will be appreciated by those of ordinary skill in the art, two sequences are generally considered to be "substantially identical" if they contain identical residues in corresponding positions. As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul, et al., Basic local alignment search tool, *J. Mol. Biol.,* 215(3): 403-410, 1990; Altschul, et al., *Methods in Enzymology;* Altschul et al., *Nucleic Acids Res.* 25:3389-3402, 1997; Baxevanis et al., *Bioinformatics A Practical Guide to the Analysis of Genes and Proteins,* Wiley, 1998; and Misener, et al., (eds.), *Bioinformatics Methods and Protocols* (Methods in Molecular Biology, Vol. 132), Humana Press, 1999. In addition to identifying identical sequences, the programs mentioned above typically provide an indication of the degree of identity. In some embodiments, two sequences are considered to be substantially identical if at least 50%, 55%, 60%, 65%, 70%, 75%, 80%, 85%, 90%, 91%, 92%, 93%, 94%, 95%, 96%, 97%, 98%, 99% or more of their corresponding residues are identical over a relevant stretch of residues. In some embodiments, the relevant stretch is a complete sequence. In some embodiments, the relevant stretch is at least 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500 or more residues.

Therapeutic moiety: As used herein, the term "therapeutic moiety" refers to a portion of a molecule that renders the therapeutic effect of the molecule. In some embodiments, a therapeutic moiety is a polypeptide having therapeutic activity. For example, a therapeutic moiety according to the present invention can be a polypeptide that can substitute for a natural FXN protein. In some embodiments, a therapeutic moiety according to the present invention can be a polypeptide that can rescue one or more phenotypes associated with FXN deficiency. In some embodiments, a therapeutic moiety according to the present invention can treat one or more symptoms in a FRDA patient.

Therapeutically effective amount: As used herein, the term "therapeutically effective amount" refers to an amount of a therapeutic mitochondrial protein (e.g., FXN) which confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). In particular, the "therapeutically effective amount" refers to an amount of a therapeutic protein or composition effective to treat, ameliorate, or prevent a desired disease or condition, or to exhibit a detectable therapeutic or preventative effect, such as by ameliorating symptoms associated with the disease, preventing or delaying the onset of the disease, and/or also lessening the severity or frequency of symptoms of the disease. A therapeutically effective amount is commonly administered in a dosing regimen that may comprise multiple unit doses. For any particular therapeutic protein, a therapeutically effective amount (and/or an appropriate unit dose within an effective dosing regimen) may vary, for example, depending on route of administration, on combination with other pharmaceutical agents. Also, the specific therapeutically effective amount (and/or unit dose) for any particular patient may depend upon a variety of factors including the disorder being treated and the severity of the disorder; the activity of the specific pharmaceutical agent employed; the specific composition employed; the age, body weight, general health, sex and diet of the patient; the time of administration, route of administration, and/or rate of excretion or metabolism of the specific fusion protein employed; the duration of the treatment; and like factors as is well known in the medical arts.

Treatment: As used herein, the term "treatment" (also "treat" or "treating") refers to any administration of a therapeutic protein (e.g., mitochondrial protein) that partially or completely alleviates, ameliorates, relieves, inhibits, delays onset of, reduces severity of and/or reduces incidence of one or more symptoms or features of a particular disease, disorder, and/or condition (e.g., FRDA). Such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition.

DETAILED DESCRIPTION

The present invention provides, among other things, compositions and methods for treatment of Friedrich's Ataxia based on effective targeting of a therapeutic moiety to mitochondria that can substitute for natural FXN protein activity or rescue one or more phenotypes or symptoms associated with FXN-deficiency. In some embodiments, the present invention provides a targeted therapeutic comprising a therapeutic moiety, which is a polypeptide having an N-terminus and a C-terminus, a mitochondrial targeting sequence associated with the therapeutic moiety at the N-terminus, and a mitochondrial membrane-penetrating peptide associated with the therapeutic moiety at the C-terminus, wherein the therapeutic moiety is targeted to mitochondria upon cellular entry.

Various aspects of the invention are described in detail in the following sections. The use of sections is not meant to limit the invention. Each section can apply to any aspect of the invention. In this application, the use of "or" means "and/or" unless stated otherwise.

Targeted Therapeutics

Typically, a targeted therapeutic according to the present invention includes a therapeutic moiety, a mitochondrial targeting sequence and/or a mitochondrial membrane-penetrating peptide. In some embodiments, a mitochondrial targeting sequence and/or a mitochondrial membrane-penetrating peptide is an intrinsic part of a therapeutic moiety.

Therapeutic Moiety

A therapeutic moiety suitable for the present invention can be any molecular or a portion of a molecule that can substitute for naturally-occurring FXN protein activity or rescue one or more phenotypes or symptoms associated with frataxin-deficiency once located to mitochondria. In some embodiments, a therapeutic moiety suitable for the invention is a polypeptide having an N-terminus and a C-terminus and an amino acid sequence substantially similar or identical to mature human FXN protein.

Typically, human FXN is produced as a precursor molecule that is processed to a mature form within mitochondria (Condo et al. Human Mol Genet 16:1534 2007). This process generally occurs in two steps, yielding an intermediate and mature form of the protein (Schmucker et al. Human Mol Genet 17:3521 2008). Typically, the precursor form is also referred to as full-length precursor or full-length FXN protein, which contains 210 amino acids. The N-terminal 55 amino acids are cleaved once the precursor is located within mitochondria, resulting in an immature or intermediate form known as FXN 56-210. This intermediate form is further processed to the mature form, defined as FXN 81-210. Thus, it is contemplated that the N-terminal 80 amino acids contains mitochondrial targeting sequence and is generally not required for the FXN protein activity. Mapping of this N terminal domain using truncation mutants has identified the first 20 amino acids of the N terminus to be sufficient to induce mitochondrial targeting. These N-terminal 20 amino acids are also referred to as N-terminal mitochondrial targeting sequence. The amino acid sequences of the mature form (SEQ ID NO:1), N-terminal mitochondrial targeting sequence (SEQ ID NO:2), the N-terminal 80 amino acids including the mitochondrial targeting sequence (SEQ ID NO:3), and full-length precursor (SEQ ID NO:4) of a typical wild-type or naturally-occurring human FXN protein are shown in Table 1.

TABLE 1

Human Frataxin (FXN) (Q16595)

| | |
|---|---|
| Mature Form | SGTLGHPGSLDETTYERLAEETLDSLAEFFEDLAD KPYTFEDYDVSFGSGVLTVKLGGDLGTYVINKQTP NKQIWLSSPSSGPKRYDWTGKNWVYSHDGVSLHEL LAAELTKALKTKLDLSSLAYSGKDA (SEQ ID NO: 1) |
| N-terminal Mitochondrial Targeting sequence | MWTLGRRAVAGLLASPSPAQ (SEQ ID NO: 2) |
| N-terminal 80 residues | MWTLGRRAVAGLLASPSPAQAQTLTRVPRPAELAP LCGRRGLRTDIDATCTPRRASSNQRGLNQIWNVKK QSVYLMNLRK (SEQ ID NO: 3) |
| Full-Length Precursor | MWTLGRRAVAGLLASPSPAQAQTLTRVPRPAELAP LCGRRGLRTDIDATCTPRRASSNQRGLNQIWNVKK QSVYLMNLRKSGTLGHPGSLDETTYERLAEETLDS LAEFFEDLADKPYTFEDYDVSFGSGVLTVKLGGDL GTYVINKQTPNKQIWLSSPSSGPKRYDWTGKNWVY SHDGVSLHELLAAELTKALKTKLDLSSLAYSGKDA (SEQ ID NO: 4) |

Thus, in some embodiments, a therapeutic moiety suitable for the present invention is mature human FXN protein (SEQ ID NO:1). In some embodiments, a suitable therapeutic moiety may be a homologue or an analogue of mature human FXN protein. For example, a homologue or an analogue of mature human FXN protein may be a modified mature human FXN protein containing one or more amino acid substitutions, deletions, and/or insertions as compared to a wild-type or naturally-occurring FXN protein (e.g., SEQ ID NO:1), while retaining substantial FXN protein activity. Thus, in some embodiments, a therapeutic moiety suitable for the present invention is substantially homologous to mature human FXN protein (SEQ ID NO:1). In some embodiments, a therapeutic moiety suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more homologous to SEQ ID NO:1. In some embodiments, a therapeutic moiety suitable for the present invention is substantially identical to mature human FXN protein (SEQ ID NO:1). In some embodiments, a therapeutic moiety suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more identical to SEQ ID NO:1. In some embodiments, a therapeutic moiety suitable for the present invention contains a fragment or a portion of mature human FXN protein.

Alternatively, a therapeutic moiety suitable for the present invention is full-length FXN protein. In some embodiments, a suitable therapeutic moiety may be a homologue or an analogue of full-length human FXN protein. For example, a homologue or an analogue of full-length human FXN protein may be a modified full-length human FXN protein containing one or more amino acid substitutions, deletions, and/or insertions as compared to a wild-type or naturally-occurring full-length FXN protein (e.g., SEQ ID NO:4), while retaining substantial FXN protein activity. Thus, In some embodiments, a therapeutic moiety suitable for the present invention is substantially homologous to full-length human FXN protein (SEQ ID NO:4). In some embodiments, a therapeutic moiety suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more homologous to SEQ ID NO:4. In some embodiments, a therapeutic moiety suitable for the present invention is substantially identical to SEQ ID NO:4. In some embodiments, a therapeutic moiety suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more identical to SEQ ID NO:4. In some embodiments, a therapeutic moiety suitable for the present invention contains a fragment or a portion of full-length human FXN protein. As used herein, a full-length FXN protein typically contains an intrinsic mitochondrial targeting sequence.

Mitochondrial Targeting Sequence

In some embodiments, a therapeutic moiety is associated with a mitochondrial targeting sequence. A mitochondrial targeting sequence suitable for the present invention can be any peptide, or the like, that is capable of directing a therapeutic moiety to the mitochondrion of a cell. Many mitochondrial proteins contain an intrinsic mitochondrial targeting sequence, typically, at the N-terminus Thus, a suitable mitochondrial targeting sequence may be derived from such intrinsic mitochondrial targeting sequence of mitochondrial proteins including, but not limited to, the FXN protein, cytochrome C oxidase IV (Cox IV) protein, ornithine transcarbylamse (OTC) protein, lipoamide dehydrogenase (LAD) protein, and malate dehydrogenase (MDH) protein. Suitable mitochondrial targeting sequences encompass both naturally-occurring sequences and modified sequences that retain mitochondrial targeting ability and can be produced using recombinant and synthetic methods or purified from natural sources.

In some embodiments, a mitochondrial targeting sequence suitable for the present invention is or includes the N-terminal 20 amino acids of the full-length FXN protein (SEQ ID NO:2). In some embodiments, a mitochondrial targeting sequence suitable for the present invention is substantially homologous to SEQ ID NO:2. In some embodiments, a suitable mitochondrial targeting sequence has a sequence at least 50%, 55%, 60%, 65%, 70%, 75%, 80%, 85%, 90%, 91%, 92%, 93%, 94%, 95%, 96%, 97%, 98%, 99% or more homologous to SEQ ID NO:2. In some embodiments, a suitable mitochondrial targeting sequence has a sequence at least 50%, 55%, 60%, 65%, 70%, 75%, 80%, 85%, 90%, 91%, 92%, 93%, 94%, 95%, 96%, 97%, 98%, 99% or more identical to SEQ ID NO:2.

In some embodiments, a mitochondrial targeting sequence suitable for the present invention is or includes the N-terminal 80 amino acids of the full-length FXN protein (SEQ ID NO:3). In some embodiments, a mitochondrial targeting sequence suitable for the present invention is substantially homologous to SEQ ID NO:3. In some embodiments, a suitable mitochondrial targeting sequence has a sequence at least 50%, 55%, 60%, 65%, 70%, 75%, 80%, 85%, 90%, 91%, 92%, 93%, 94%, 95%, 96%, 97%, 98%, 99 or more homologous to SEQ ID NO:3. In some embodiments, a suitable mitochondrial targeting sequence has a sequence at least 50%, 55%, 60%, 65%, 70%, 75%, 80%, 85%, 90%, 91%, 92%, 93%, 94%, 95%, 96%, 97%, 98%, 99% or more identical to SEQ ID NO:3.

It is contemplated that a mitochondrial targeting sequence may be associated with a therapeutic moiety (e.g., a FXN protein) in any manner. For example, a mitochondrial targeting sequence may be intrinsically present in a therapeutic moiety (such as the N-terminal 20 amino acids of the full-length human FXN protein). In some embodiments, a mitochondrial targeting sequence can be conjugated to a therapeutic moiety via a chemical link at the N-terminus, C-terminus and/or internally. In some embodiments, a mitochondrial targeting sequence is fused to a therapeutic moiety in a fusion protein configuration such that the mitochondrial targeting sequence is present at the N-terminus, C-terminus and/or internally. In particular embodiments, a mitochondrial targeting sequence is fused to a therapeutic moiety at the N-terminus. In some embodiments, a mitochondrial targeting sequence may be associated with a therapeutic moiety (e.g., a FXN protein) directly or indirectly via a linker or spacer (e.g., a chemical or peptide linker or spacer).

Mitochondrial Membrane-Penetrating Peptide

Typically, a therapeutic moiety is associated with a mitochondrial membrane-penetrating peptide. A mitochondrial membrane-penetrating peptide suitable for the present invention can be any peptide or the like that is capable of directing a protein to penetrate the mitochondrial membrane within a cell. In many embodiments, mitochondrial membrane penetrating peptides are also capable of penetrating cell membrane. Such mitochondrial membrane penetrating peptides are particularly useful for the present invention. Thus, in this application, a "mitochondrial membrane-penetrating peptide" is also referred to as "a mitochondrial penetrating peptide," "a cell membrane-penetrating peptide," or "a cell penetrating peptide."

Exemplary mitochondrial membrane penetrating peptides include, but are not limited to, HIV-TAT, Antp, penetratin, polylysine, polyarginine, VP22, Syn B1, PTD-4, Pep-1, transportan and FGF-4 peptides. Suitable mitochondrial membrane penetrating peptides encompass both naturally-occurring peptides and modified peptides that retain mitochondrial penetrating ability and can be produced using recombinant and synthetic methods or purified from natural sources.

In some embodiments, a mitochondrial penetrating peptide suitable for the present invention is or include a sequence derived from HIV-TAT peptide. In some embodiments, a suitable mitochondrial penetrating peptide is or includes HIV-TAT peptide sequence GYGRKKRRQRRR (SEQ ID NO:5). In some embodiments, a suitable mitochondrial penetrating peptide contains an amino acid sequence substantially homologous to HIV-TAT peptide sequence GYGRKKRRQRRR (SEQ ID NO:5). For example, a suitable mitochondrial penetrating peptide may contain a sequence that includes at least 3 (e.g., at least 4, at least 5, at least 6, at least 7, at least 8, at least 9, at least 10, at least 11, or at least 12) amino acids that appear in HIV-TAT peptide GYGRKKRRQRRR (SEQ ID NO:5). In some embodiments, the at least 3 (e.g., at least 4, at least 5, at least 6, at least 7, at least 8, at least 9, at least 10, at least 11, or at least 12) amino acids maintain their relative positions and/or spacing as they appear in HIV-TAT peptide GYGRKKRRQRRR (SEQ ID NO:5). In some embodiments, a suitable mitochondrial targeting sequence has a sequence at least 50%, 55%, 60%, 65%, 70%, 75%, 80%, 85%, 90%, 91%, 92%, 93%, 94%, 95%, 96%, 97%, 98%, 99% or more homologous to SEQ ID NO:5.

As described in the Examples section, a mitochondrial penetrating sequence present at the C-terminus of a therapeutic moiety is surprisingly effective to target the therapeutic moiety to mitochondria. However, it is contemplated that a mitochondrial penetrating sequence may be located at various other places, for example, at the N-terminus, the C-terminus or internally.

It will be appreciated that the mitochondrial membrane-penetrating peptide may be associated with a therapeutic moiety (e.g., a FXN protein) in any manner. For example, in some embodiments, a mitochondrial membrane-penetrating peptide is conjugated to a therapeutic moiety. In some embodiments, a mitochondrial membrane-penetrating peptide is fused to a therapeutic moiety in a fusion protein configuration. In some embodiments, a mitochondrial membrane-penetrating peptide may be associated with a therapeutic moiety (e.g., a FXN protein) directly or indirectly via a linker or spacer (e.g., a chemical or peptide linker or spacer). In some embodiments, a mitochondrial membrane-penetrating peptide may be intrinsically present in a therapeutic moiety.

Production of Targeted Therapeutics

A targeted therapeutic according to the invention may be produced by any available means. As described above, a typical targeted therapeutic according to the present invention contains a therapeutic moiety (e.g., a FXN protein), a mitochondrial targeting sequence, and a mitochondrial membrane-penetrating peptide. Each moiety (i.e., the therapeutic moiety, the mitochondrial targeting sequence, and/or the mitochondrial membrane-penetrating peptide) may be separately prepared and then conjugated via various means known in the art. Each moiety may be recombinantly produced, chemically synthesized or purified from natural sources.

In some embodiments, a targeted therapeutic containing a therapeutic moiety (e.g., a FXN protein), a mitochondrial targeting sequence, and a mitochondrial membrane-penetrating peptide may be produced as a fusion protein, i.e., a targeted therapeutic fusion protein. In some embodiments, a targeted therapeutic fusion protein contains a mitochondrial targeting sequence at the N-terminus followed by a therapeutic moiety (e.g., mature human FXN protein) and a mitochondrial membrane-penetrating peptide at the C-terminus. In some embodiments, a targeted therapeutic fusion protein contains an amino acid sequence as shown below (SEQ ID NO:6). The mitochondrial targeting sequence is underlined and the mitochondrial membrane-penetrating peptide is bolded.

(SEQ ID NO: 6)
<u>MWTLGRRAVAGLLASPSPAQAQTLTRVPRPAELAPLCGRRGLRTDIDATC</u>

TPRRASSNQRGLNQIWNVKKQSVYLMNLRKSGTLGHPGSLDETTYERLAE

ETLDSLAEFFEDLADKPYTFEDYDVSFGSGVLTVKLGGDLGTYVINKQTP

NKQIWLSSPSSGPKRYDWTGKNWVYSHDGVSLHELLAAELTKALKTKLDL

SSLAYSGKDAGYGRKKRRQRRR

In some embodiments, a targeted therapeutic fusion protein according to the invention is a homologue or an analogue of SEQ ID NO:6 that contains one or more amino acid substitutions, deletions, and/or insertions. In some embodiments, a targeted therapeutic fusion protein according to the invention contains an amino acid sequence substantially homologous to SEQ ID NO:6. In some embodiments, a suitable targeted therapeutic fusion protein has a sequence at least 50%, 55%, 60%, 65%, 70%, 75%, 80%, 85%, 90%, 91%, 92%, 93%, 94%, 95%, 96%, 97%, 98%, 99° or more homologous to SEQ ID NO:6. In some embodiments, a suitable targeted therapeutic fusion protein has a sequence at least 50%, 55%, 60%, 65%, 70%, 75%, 80%, 85%, 90%, 91%, 92%, 93%, 94%, 95%, 96%, 97%, 98%, 99% or more identical to SEQ ID NO:6. Typically, a homologue or an analogue of SEQ ID NO:6 retains substantial therapeutic activity.

In some embodiments, targeted therapeutic fusion proteins described herein are recombinantly produced using various expression systems known in the art. To give but a few examples, known expression systems include, but are not limited to, bacteria, egg, baculovirus, plant, yeast, or mammalian cells.

In some embodiments, targeted therapeutic fusion proteins according to the present invention are produced in bacterial cells. Non-limiting examples of bacterial cells that may be used in accordance with the present invention include *E. coli, Bacillus brevis, Bacillus megatrerium, Bacillus subtilis*, and *Caulobacter crescentus*, among others.

There are methods known to those of skill in the art that are suitable for use with recombinant protein expression methods, for example, to reduce possible proteolytic degradation of proteins, protein misfolding, and poor protein solubility. For example, fusion technology may be employed, wherein a target protein is fused to a fusion partner to facilitate target protein expression. Fusion partners that may be used include, for example, maltose binding protein, glutathione-S-transferase, thioredocin, NUS A, ubiquitin, and small ubiquitin-related modifier (SUMO). In some embodiments, yeast SUMO fusion technology is used.

In some embodiments, targeted therapeutic fusion proteins according to the present invention are produced in mammalian cells. Non-limiting examples of mammalian cells that may be used in accordance with the present invention include BALB/c mouse myeloma line (NSO/l, ECACC No: 85110503); human retinoblasts (PER.C6, Cru-Cell, Leiden, The Netherlands); monkey kidney CV1 line transformed by SV40 (COS-7, ATCC CRL 1651); human embryonic kidney line (293 or 293 cells subcloned for growth in suspension culture, Graham et al., J. Gen Virol., 36:59, 1977); human fibrosarcoma cell line (HT1080); baby hamster kidney cells (BHK, ATCC CCL 10); Chinese hamster ovary cells+/−DHFR (CHO, Urlaub and Chasin, Proc. Natl. Acad. Sci. USA, 77:4216, 1980); mouse sertoli cells (TM4, Mather, Biol. Reprod., 23:243-251, 1980); monkey kidney cells (CV1 ATCC CCL 70); African green monkey kidney cells (VERO-76, ATCC CRL-1 587); human cervical carcinoma cells (HeLa, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci., 383:44-68, 1982); MRC 5 cells; FS4 cells; and a human hepatoma line (Hep G2).

In some embodiments, targeted therapeutic fusion proteins according to the present invention are produced in avian expression systems, e.g. in eggs of chimeric chickens. Exemplary methodologies for expressing proteins in avian expression systems are described in PCT Publication WO 2004/015123 and U.S. Pub. Nos. 20060191026, 20090178147; 20090180989; 20100083389; and 2010033219, the entire contents of each of which are incorporated herein by reference.

In some embodiments, targeted therapeutic fusion proteins according to the present invention are produced in plant expression systems, e.g. in tobacco plants or related species (e.g., *Nicotiana* species). For example, fusion proteins may be expressed in *Nicotiana benthamiana*. Exemplary methodologies for expressing proteins in plant expression systems are known in the art. For example, GENEWARE® technology utilizes a modified tobacco mosaic virus vector to express heterologous proteins within a tobacco plant. Expressed proteins may subsequently be isolated and/or purified.

In some embodiments, targeted therapeutic fusion proteins according to the present invention are produced in yeast expression systems, e.g. in methylotrophic yeast. In some embodiments, fusion proteins are expressed in *Pichia pastoris*. Exemplary methodologies for expressing proteins in yeast expression systems are known in the art (see, for example, Daly, et al. J Mol Recognit. 18:119 (2005), the contents of which is incorporated herein by reference).

It will be appreciated that other expression systems are known in the art and can be used to produce targeted therapeutics described herein.

Among other things, the present invention also provides nucleic acids encoding various therapeutic fusion proteins described herein, vectors containing nucleic acids and host expression systems (e.g., bacteria, egg, baculovirus, plant, yeast, or mammalian cells) containing vectors according to the invention. In some embodiments, a nucleic acid or vector suitable for the invention may also be constructed to encode a tag (e.g., a His tag) to be fused to a therapeutic fusion protein to facilitate purification. An exemplary fusion protein construct is described in Example 1 and illustrated in FIG. 1.

Treatment of Friedreich's Ataxia (FRDA)

Friedreich's Ataxia (FRDA) is a rare, autosomal recessive degenerative neuromuscular disease that results from diminished levels of the mitochondrial protein frataxin (FXN) and typically leads to degeneration of the large sensory neurons and spinocerebellar tracts, cardiomyopathy, and increased incidence of diabetes.

Individuals affected by FRDA typically have mild to severe muscular impairments, including ataxia, fatigue, muscle loss, blurring of vision, and slurring of speech. In many cases, individuals affected by FRDA develop severe and life threatening cardiomyopathies and are susceptible to FRDA associated diabetes mellitus. Death usually occurs between 35 to 40 years of age in individuals affected by FRDA.

Many of the individuals affected by FRDA have identifiable mutations in the FXN gene. The most common mutation in the FXN gene, which is seen in over 95% of patients, is a GAA triplet repeat expansion within the first intron of the FXN gene, leading to inhibition of transcriptional initiation and elongation. A few FRDA patients are compound heterozygotes for the triplet expansion and for a point mutation in the FXN gene.

Compositions and methods of the present invention may be used to effectively treat individuals suffering from or susceptible to FRDA. The terms, "treat" or "treatment," as used herein, refers to amelioration of one or more symptoms associated with the disease, prevention or delay of the onset of one or more symptoms of the disease, and/or lessening of the severity or frequency of one or more symptoms of the disease.

In some embodiments, treatment refers to partially or completely alleviation, amelioration, relief, inhibition, delaying onset, reducing severity and/or incidence of neuromuscular impairment in an FRDA patient. As used herein, the term "neuromuscular impairment" includes various symptoms associated with impairment of the central nervous system (e.g., the brain and spinal cord) or the peripheral nervous system (e.g., muscles, the neuromuscular junction, peripheral nerves in the limbs and the motor-nerve cells in the spinal cord). Symptoms of neuromuscular impairment may include, for example, atrophy (e.g., of the cervical spinal cord), increased or decreased tone, loss of muscle bulk, weakness, muscle twitching, cramping, numbness and tingling, droopy eyelids, double vision, weakness that worsens with activity, difficulty swallowing, and difficulty in breathing, among others. In some embodiments, treatment refers to partial or complete alleviation, relief, inhibition, delaying onset, reducing severity and/or incidence of cardiac hypertrophy in an FRDA patient. Generally, the term "cardiac hypertrophy", as used herein, refers to a thickening of the heart muscle (myocardium). In some embodiments, cardiac hypertrophy results in a decrease in size of the chamber of the heart, including the left and right ventricles. Thus, in some embodiments, treatment refers to decreased progression of atrophy (e.g., of the cervical spinal cord). In certain embodiments, progression of atrophy (e.g., of the cervical spinal cord) is decreased by about 5%, 10%, 15%, 20%, 25%, 30%, 35%, 40%, 45%, 50%, 55%, 60%, 65%, 70%, 75%, 80%, 85%, 90%, 95%, 100% or more as compared to a control. In some embodiments, treatment refers to decreased progression of cardiac hypertrophy. In certain embodiments, progression of cardiac hypertrophy is decreased by about 5%, 10%, 15%, 20%, 25%, 30%, 35%, 40%, 45%, 50%, 55%, 60%, 65%, 70%, 75%, 80%, 85%, 90%, 95%, 100% or more as compared to a control.

It will be appreciated that tissue analyses may be performed by any appropriate method available in the art and/or described herein. For example, in some embodiments, tissues are analyzed by magnetic resonance imaging (MRI). Additional tissue analysis methods include, but are not limited to, computed tomography (CT), positron emission tomography (PET), tissue biopsy, biochemical tests of enzyme function (e.g., in tissue or in serum), ultrasound, or combinations thereof. It will be appreciated that cardiac function may be performed by any appropriate method available in the art and/or described herein. For example, in some embodiments, cardiac function is analyzed by electrocardiogram, holter monitoring, event monitoring, cardiac stress test, electrophysiology, coronary catheterization, echocardiogram, intravascular ultrasound, positron emission tomography (PET), computed tomography angiography (CTA), magnetic resonance imaging (MRI), among others.

In some embodiments, treatment refers to partial or complete alleviation, relief, inhibition, delaying onset, reducing severity and/or incidence of metabolic disorders, e.g., diabetes mellitus, in an FRDA patient. It will be appreciated that metabolic analyses may be performed on any appropriate biological sample and by any appropriate method available in the art and/or described herein. For example, in some embodiments, metabolic function is analyzed in tissue. In some embodiments, metabolic function is analyzed in serum. In some embodiments, enzyme function, protein levels, and/or electrolytes are analyzed. In some embodiments, levels of iron accumulation in mitochondria are analyzed. In some embodiments, serum glucose, calcium, human serum albumin, serum total protein, sodium, potassium, carbon dioxide, chloride, blood urea nitrogen, creatinine, alkaline phosphatase, alanine amino transferase, aspartate amino transferase, bilirubin, and combinations thereof, are analyzed. In some embodiments, treatment refers to decreased incidence of metabolic disorders, such as diabetes mellitus. In certain embodiments, incidence of metabolic disorders is decreased by about 5%, 10%, 15%, 20%, 25%, 30%, 35%, 40%, 45%, 50%, 55%, 60%, 65%, 70%, 75%, 80%, 85%, 90%, 95%, 100% or more as compared to a control. In some embodiments, treatment refers to decreased iron accumulation in mitochondria in relevant tissues. In certain embodiments, iron accumulation in relevant tissues is decreased by about 5%, 10%, 15%, 20%, 25%, 30%, 35%, 40%, 45%, 50%, 55%, 60%, 65%, 70%, 75%, 80%, 85%, 90%, 95%, or 100% as compared to a control. In some embodiments, treatment refers to increased enzyme activity or protein level of FXN in relevant tissues. In certain embodiments, FXN activity or protein level in relevant tissues is decreased by about 5%, 10%, 15%, 20%, 25%, 30%, 35%, 40%, 45%, 50%, 55%, 60%, 65%, 70%, 75%, 80%, 85%, 90%, 95%, or 100% as compared to a control.

In some embodiments, treatment refers to improvement in iron sulfur cluster enzyme level and/or function. For example, treatment can result in increased level and/or function of one or more iron cluster enzymes. It will be appreciated that any iron sulfur cluster enzyme may be improved such as, for example, aconitase, succinate dehydrogenase, among others. In some embodiments, treatment according to the present invention results in increased level and/or function of an iron sulfur cluster enzyme in a patient by more than about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 105%, about 110%, about 115%, about 120%, about 125%, about 130%, about 135%, about 140%, about 145%, about 150%, about 155%, about 160%, about 165%, about 170%, about 175%, about 180%, about 185%, about 190%, about 195%, about 200% or more, as compared to the average level and/or function of the iron sulfur cluster enzyme in the patient before the treatment or of one or more control individuals with similar disease without treatment.

In some embodiments, treatment refers to increased survival (e.g. survival time). For example, treatment can result in an increased life expectancy of a patient. In some embodiments, treatment according to the present invention results in an increased life expectancy of a patient by more than about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 105%, about 110%, about 115%, about 120%, about 125%, about 130%, about 135%, about 140%, about 145%, about 150%, about 155%, about 160%, about 165%, about 170%, about 175%, about 180%, about 185%, about 190%, about 195%, about 200% or more, as compared to the average life expectancy of one or more control individuals with similar disease without treatment. In some embodiments, treatment according to the present invention results in an increased life expectancy of a patient by more than about 6 month, about 7 months, about 8 months, about 9 months, about 10 months, about 11 months, about 12 months, about 2 years, about 3 years, about 4 years, about 5 years, about 6 years, about 7 years, about 8 years, about 9 years, about 10 years or more, as compared to the average life expectancy of one or more control individuals with similar disease without treatment. In some embodiments, treatment according to the present invention results in long term survival of a patient. As used herein, the term "long term survival" refers to a survival time or life expectancy longer than about 40 years, 45 years, 50 years, 55 years, 60 years, or longer.

The terms, "improve," "increase" or "reduce," as used herein, indicate values that are relative to a control. In some embodiments, a suitable control is a baseline measurement, such as a measurement in the same individual prior to initiation of the treatment described herein, or a measurement in a control individual (or multiple control individuals) in the absence of the treatment described herein. A "control individual" is an individual afflicted with FRDA, who is about the same age and/or gender as the individual being treated (to ensure that the stages of the disease in the treated individual and the control individual(s) are comparable).

The individual (also referred to as "patient" or "subject") being treated is an individual (fetus, infant, child, adolescent, or adult human) having FRDA or having the potential to develop FRDA. The individual can have residual endogenous FXN expression and/or activity, or no measurable activity. For example, the individual having FRDA may have FXN expression levels that are less than about 30-50%, less than about 25-30%, less than about 20-25%, less than about 15-20%, less than about 10-15%, less than about 5-10%, less than about 0.1-5% of normal FXN expression levels.

In some embodiments, the individual is an individual who has been recently diagnosed with the disease. Typically, early treatment (treatment commencing as soon as possible after diagnosis) is important to minimize the effects of the disease and to maximize the benefits of treatment.

Administration of FXN

A targeted therapeutic according to the present invention may be administered to a patient alone, or in compositions or medicaments comprising the targeted therapeutic (e.g., in the manufacture of a medicament for the treatment of the disease), as described herein. The compositions can be formulated with a physiologically acceptable carrier or excipient to prepare a pharmaceutical composition. The carrier and composition can be sterile. The formulation should suit the mode of administration.

Suitable pharmaceutically acceptable carriers include but are not limited to water, salt solutions (e.g., NaCl), saline, buffered saline, alcohols, glycerol, ethanol, gum arabic, vegetable oils, benzyl alcohols, polyethylene glycols, gelatin, carbohydrates such as lactose, amylose or starch, sugars such as mannitol, sucrose, or others, dextrose, magnesium stearate, talc, silicic acid, viscous paraffin, perfume oil, fatty acid esters, hydroxymethylcellulose, polyvinyl pyrolidone, etc., as well as combinations thereof. The pharmaceutical preparations can, if desired, be mixed with auxiliary agents (e.g., lubricants, preservatives, stabilizers, wetting agents, emulsifiers, salts for influencing osmotic pressure, buffers, coloring, flavoring and/or aromatic substances and the like) which do not deleteriously react with the active compounds or interference with their activity. In some embodiments, a water-soluble carrier suitable for intravenous administration is used.

The composition or medicament, if desired, can also contain minor amounts of wetting or emulsifying agents, or pH buffering agents. The composition can be a liquid solution, suspension, emulsion, tablet, pill, capsule, sustained release formulation, or powder. The composition can also be formulated as a suppository, with traditional binders and carriers such as triglycerides. Oral formulation can include standard carriers such as pharmaceutical grades of mannitol, lactose, starch, magnesium stearate, polyvinyl pyrollidone, sodium saccharine, cellulose, magnesium carbonate, etc.

The composition or medicament can be formulated in accordance with the routine procedures as a pharmaceutical composition adapted for administration to human beings. For example, in some embodiments, a composition for intravenous administration typically is a solution in sterile isotonic aqueous buffer. Where necessary, the composition may also include a solubilizing agent and a local anesthetic to ease pain at the site of the injection. Generally, the ingredients are supplied either separately or mixed together in unit dosage form, for example, as a dry lyophilized powder or water free concentrate in a hermetically sealed container such as an ampule or sachette indicating the quantity of active agent. Where the composition is to be administered by infusion, it can be dispensed with an infusion bottle containing sterile pharmaceutical grade water, saline or dextrose/water. Where the composition is administered by injection, an ampule of sterile water for injection or saline can be provided so that the ingredients may be mixed prior to administration.

A targeted therapeutic according to the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

A targeted therapeutic according to the invention (or a composition or medicament containing the same) may be administered by any appropriate route. In some embodiments, a targeted therapeutic according to the invention (or a composition or medicament containing the same) is administered intravenously. In some embodiments, a targeted therapeutic according to the invention (or a composition or medicament containing the same) is administered subcutaneously. In some embodiments, a targeted therapeutic according to the invention (or a composition or medicament containing the same) is administered by direct administration to a target tissue, such as heart or muscle (e.g., intramuscular), or nervous system (e.g., direct injection into the brain; intraventricularly; intrathecally). Alternatively, a targeted therapeutic according to the invention (or a composition or medicament containing the same) can be administered parenterally, transdermally, or transmucosally (e.g., orally or nasally). More than one route can be used concurrently, if desired.

A targeted therapeutic according to the invention (or a composition or medicament containing the same) is administered in a therapeutically effective amount (i.e., a dosage amount that, when administered at regular intervals, is sufficient to treat the disease, such as by ameliorating symptoms associated with the disease, preventing or delaying the onset of the disease, and/or also lessening the severity or frequency of symptoms of the disease, as described above). As used herein, the therapeutic effective amount is also referred to as therapeutic effective dose or therapeutic effective dosage amount. The dose which will be therapeutically effective for the treatment of the disease will depend on the nature and extent of the disease's effects, and can be determined by standard clinical techniques. In addition, in vitro or in vivo assays may optionally be employed to help identify optimal dosage ranges. The precise dose to be employed will also depend on the route of administration, and the seriousness of the disease, and should be decided according to the judgment of a practitioner and each patient's circumstances. Effective doses may be extrapolated from dose-response curves derived from in vitro or animal model test systems (e.g., as described by the U.S. Department of Health and Human Services, Food and Drug Administration, and Center for Drug Evaluation and Research in "Guidance for Industry: Estimating Maximum Safe Starting Dose in Initial Clinical Trials for Therapeutics in Adult Healthy Volunteers", *Pharmacology and Toxicology*, July 2005, the entire contents of which are incorporated herein by reference).

In some embodiments, the therapeutically effective amount can be, for example, about 0.01-25 mg/kg, about 1-20 mg/kg, about 4-20 mg/kg, about 5-15 mg/kg, about 5-10 mg/kg body weight.

The effective dose for a particular individual can be varied (e.g., increased or decreased) over time, depending on the needs of the individual. For example, in times of physical illness or stress or if disease symptoms worsen, the dosage amount can be increased.

A therapeutically effective amount of a targeted therapeutic according to the invention (or a composition or medicament containing the same) is administered at regular intervals, depending on the nature and extent of the disease's effects, and on an ongoing basis. Administration at an "interval," as used herein, indicates that the therapeutically effective amount is administered periodically (as distinguished from a one-time dose). The interval can be determined by standard clinical techniques. In some embodiments, a targeted therapeutic according to the invention (or a composition or medicament containing the same) is administered bimonthly, monthly, twice monthly, triweekly, biweekly, weekly, twice weekly, thrice weekly, or daily. The administration interval for a single individual need not be a fixed interval, but can be varied over time, depending on the needs of the individual. For example, in times of physical illness or stress or if disease symptoms worsen, the interval between doses can be decreased.

As used herein, the term "bimonthly" means administration once per two months (i.e., once every two months); the term "monthly" means administration once per month; the term "triweekly" means administration once per three weeks (i.e., once every three weeks); the term "biweekly" means administration once per two weeks (i.e., once every two weeks); the term "weekly" means administration once per week; and the term "daily" means administration once per day.

The invention additionally pertains to a pharmaceutical composition comprising a targeted therapeutic (e.g., a therapeutic fusion protein containing FXN protein), as described herein, in a container (e.g., a vial, bottle, bag for intravenous administration, syringe, etc.) with a label containing instructions for administration of the composition for treatment of Friedreich's Ataxia, such as by the methods described herein.

The invention will be further and more specifically described by the following examples. Examples, however, are included for illustration purposes, not for limitation.

EXAMPLES

Example 1: Expression of N- and C-Terminal FXN-TAT Fusion Proteins

This example demonstrates the development of a recombinant FXN protein with cell penetrating properties.

As a first step in producing a recombinant FXN molecule with cell penetrating properties, FXN-TAT fusions were created with the TAT peptide located at either the N or C terminus of the FXN molecule (referred to as "N terminal FXN-TAT" or "C terminal FXN-TAT," respectively). Fusions were constructed in small ubiquitin-related modifier (SUMO) prokaryotic expression vectors and expressed in *E. coli*. SUMO technology (Butt, et al. *Protein Expr Purif.* 2005 September; 43(1):1-9; Marblestone et al. *Protein Sci.* 2006 January; 15(1):182-9) was utilized to minimize N terminal proteolysis of recombinant FXN protein during expression and purification. FIG. 1 depicts amino acid sequences of exemplary N and C terminal FXN-TAT fusion proteins. Following cleavage of the SUMO fusion partner, full length N and C terminal FXN-TAT fusion proteins were purified on size exclusion columns FIG. 2A depicts an exemplary purification scheme used to purify the fusion proteins.

Briefly, BL21(DE3) cells were transformed with 6×His-SUMO3-TAT-FXN or 6×His-SUMO3-FXN-TAT plasmid. For each construct bacterial cultures were grown at 37° C. to an $OD_{600}$ of 0.7 (1 liter per 3 L baffle shaker flask) and protein expression was induced with 0.5 mM IPTG for 3 hr. Bacterial cells were collected by centrifugation and stored at −20° C. until bacterial lysis and protein purification. Cell pellets from bacterial expression were resuspended in Lysis Buffer (50 mM Sodium Phosphate, 300 mM Sodium Chloride, 10 mM Imidazole, 1% Igepal, pH 8.0), keeping solution chilled on ice. Generally 1 g of cell paste was resuspended in 10 mL lysis buffer supplemented with Roche Complete Mini EDTA-free Protease Inhibitor Cocktail tablets (Roche #11873580001). Bacterial cells were lysed once through a microfluidizer (Microfluidics M-100P). Lysate was cleared by centrifugation for 40 minutes at 25,000 g (14,000 RPM) using a Beckman centrifuge J2-MI. Supernatant was collected and filtered prior to IMAC. 6×His-SUMO-FXN protein was captured on NiNTA resin that was previously equilibrated with 5 column volume (CV) lysis buffer. The column was washed with at least 10 CV of Lysis Buffer, and then washed with at least 5 CV of 20 mM imidazole Wash Buffer (50 mM Sodium Phosphate, 300 mM Sodium Chloride, 20 mM Imidazole, pH 8.0). Bound protein was eluted using a gradient of 20 to 250 mM imidazole over 10 CV, and collecting 10 mL fractions. Elution fractions were analyzed by Bradford assay, and Coomassie-stained gels. Clean peak fractions were pooled and transferred to dialysis tubing with 10 kDa MWCO for buffer exchange into SUMO Protease Cleavage Buffer (50 mM Sodium Phosphate, 300 mM Sodium Chloride, 10 mM Imidazole, pH 8.0), overnight at RT. 6×His-SUMO3-FXN was treated with SUMO protease 2 enzyme (LifeSensors, Inc., Malvern, Pa.) at a concentration of 4 units/mg substrate overnight at 4° C. Cleavage was confirmed by SDS-PAGE. Uncleaved protein, 6×His-SUMO, and 6×His-protease were removed by batch method using NiNTA resin.

FXN-TAT was purified further by cation exchange chromatography using SP-FF resin (GE Healthcare #17-0729-01). A 40 mL prepacked column was pre-equilibrated with binding buffer (50 mM sodium phosphate, 100 mM NaCl, pH 8.0) prior to loading supernatant after NiNTA batch binding. TAT-tagged FXN protein was eluted by gradient (100 mM→1M NaCl). Peak fractions were pooled and buffer exchanged by dialysis against 1×PBS, pH 7.4 (Fisher# BP399-1). TAT-tagged FXN was then concentrated up to 4 mg/mL, sterile filtered, and stored at −80° C.

Recombinant protein purified according to methods described herein was routinely greater than 95% pure, both by SDS-PAGE analysis (FIG. 2B) and reverse phase HPLC (data not shown).

Example 2: Mitochondrial Trafficking of N and C Terminal FXN-TAT Fusion Proteins Experiments described in this example demonstrate that recombinant C terminal FXN-TAT fusion protein can effectively traffic to mitochondria of cells. By contrast, the N-terminal fusion protein could not traffic to the mitochondria. This discovery is surprising and unexpected from the teachings in the prior art.

Specifically, following purification of FXN-TAT fusion proteins, as described in Example 1, fusion proteins were characterized in a series of cell based assays. Initially, intracellular trafficking of each of the N and C terminal FXN-TAT fusions was investigated by directly electroporating the respective protein into the cytoplasm of NC6 SV40 cells. FXN staining was quantified 48 hours following protein electroporation via immunofluorescence and confocal imaging, using the human specific anti-FXN monoclonal antibody 18A5DB1.

NC6 SV40 cells are an engineered cell line described previously (see, for example, Calmels, et al. *PLoS One*, 2009 Jul. 24; 4(7): e6379). In brief, these cells are FXN heterozygotes in which the remaining FXN allele is flanked by loxP sites, allowing for complete deletion of genomic FXN upon addition of CRE recombinase. NC6 SV40 cells were grown in complete DMEM (GIBCO/Invitrogen, Carlsbad, Calif.) supplemented with 10% heat inactivated fetal bovine serum, L-glutamine, penicillin and streptomycin.

For imaging experiments, cells were fixed in 3.7% paraformaldehyde, permeabilized in 0.2% Triton-X-100/PBS for five minutes, and blocked in PBS supplemented with 5% normal goat serum, 0.05% Triton-X-100, and 50 mM ammonium chloride. FXN staining was performed with anti-human FXN clone 18A5DB1 (Mitosciences, Eugene, Ore). Mitochondria were stained with Mitotracker Red CMX Rosamine (Invitrogen/Molecular Probes). Secondary antibodies used were Alexa conjugated goat anti-mouse monoclonals (Invitrogen/Molecular Probes). Nuclei were counterstained with Hoechst 3342 dye (Invitrogen/Molecular Probes). Imaging was performed on a Leica SP5 laser scanning confocal microscope. Images were acquired in sequential scanning mode to minimize spectral overlap.

Figure 3:
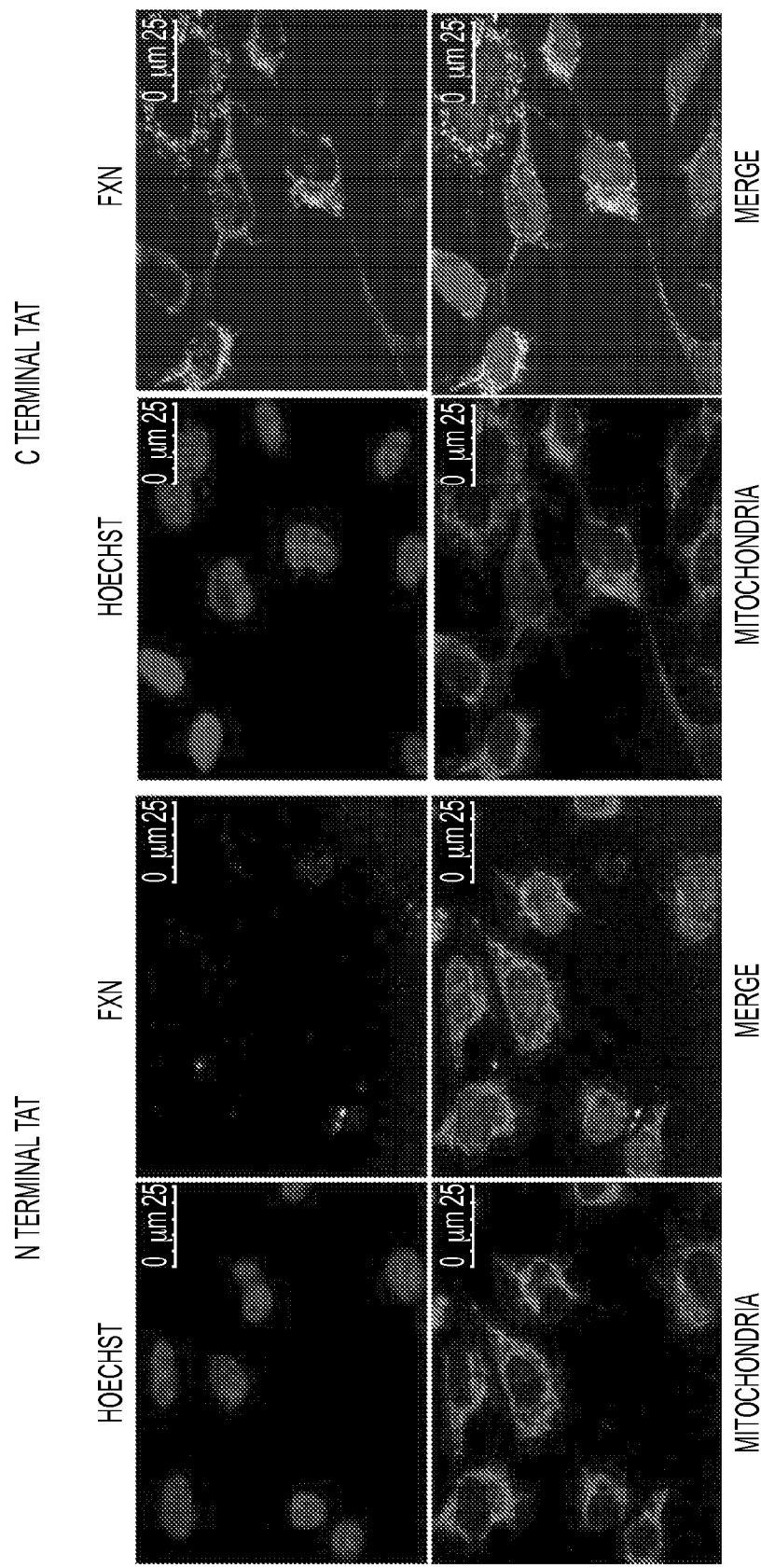
FIG. 3 depicts exemplary results illustrating localization of C-terminal and N-terminal FXN-TAT fusion proteins in mouse fibroblasts following direct electroporation of the protein into cells. NC6 SV40 mouse fibroblasts (e.g., described in Calmels N, Schmucker S, Wattenhofer-Donze M, Martelli A, Vaucamps N, et al. (2009) The First Cellular Models Based on Frataxin Missense Mutations That Reproduce Spontaneously the Defects Associated with Friedreich Ataxia. PLoS ONE 4(7): e6379) were electroporated with 10 µg of N- or C-terminal recombinant human FXN-TAT using the Amaxa Nucleofector. Following electroporation, cells were washed twice in HBSS to remove non-incorporated protein and plated on collagen coated cover-slips. Cells were allowed to adhere overnight. The following day, cells were treated with 200 nM Mitotracker Red CMX Rosamine for thirty minutes to stain mitochondria, then fixed and processed for anti-frataxin immunofluorescent staining using monoclonal antibody 18A5DB1 (from Mitosciences, specific for human frataxin). C-terminal FXN-TAT fusion proteins accumulated in the mitochondria of cells, while N-terminal FXN-TAT fusion proteins did not. Without wishing to be bound by any particular theory, N-terminal FXN-TAT fusion proteins that did not accumulate in the mitochondria of cells were presumably degraded by intracellular proteases or through the ubiquitin/proteasome pathway.

As depicted in FIG. 3, the C terminal FXN-TAT fusion was found within cells and localized to the mitochondria. Surprisingly, staining for the N terminal fusion protein was negative. Without wishing to be bound by any particular theory, we interpret these results to indicate that the N terminal fusion protein did not traffic to the mitochondria and was degraded by the cell's endogenous intracellular proteases. A possible explanation for this finding is that the FXN mitochondrial targeting sequence is encoded at the N terminus of the molecule. It is possible that fusion of the TAT peptide to the same terminus containing the mitochondrial targeting sequence may impair or render ineffective mitochondrial trafficking of the fusion protein.

Figure 4:
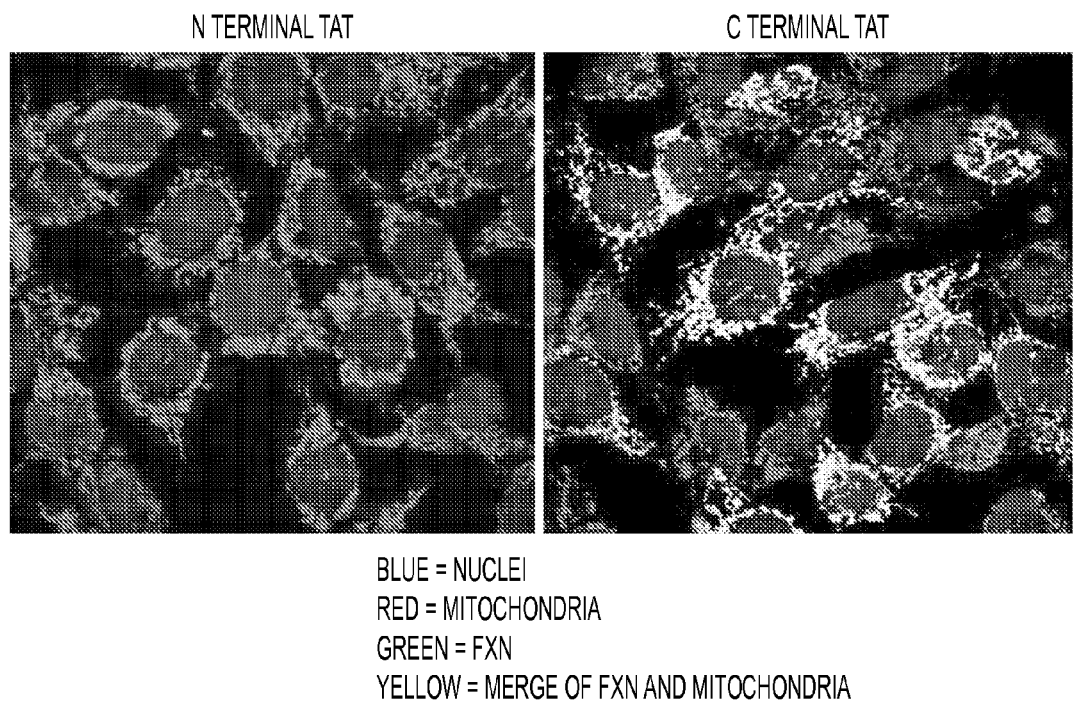
FIG. 4 depicts exemplary results illustrating localization of C-terminal and N-terminal FXN-TAT fusion proteins in mouse fibroblasts following exogenous addition of protein directly to cell culture media. NC6 SV40 mouse fibroblasts were plated overnight on collagen coated cover-slips. The following day, C- or N-terminal FXN-TAT was added directly to cell culture media at a final concentration of 2.5 µM. Cells were treated with protein for four hours, following which they were trypsinized to remove non-incorporated protein and replated onto collagen coated cover-slips. Cells were allowed to adhere overnight. The following day, cells were treated with 200 nM Mitotracker Red CMX Rosamine for thirty minutes to stain mitochondria, then fixed and processed for anti-FXN immunofluorescent staining using monoclonal antibody 18A5DB1 (from Mitosciences, specific for human FXN). C-terminal FXN-TAT fusion proteins accumulated in the mitochondria of cells, while N-terminal FXN-TAT fusion proteins did not.
Figure 6:
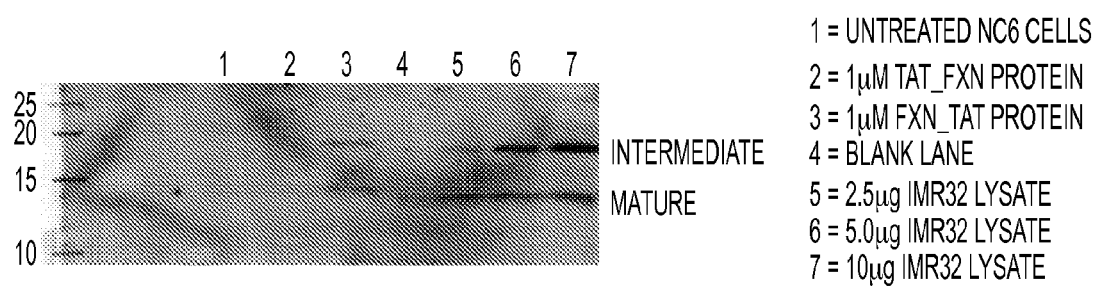
FIG. 6 depicts exemplary Western blot analysis of mouse fibroblast cells following exogenous addition of C-terminal or N-terminal FXN-TAT fusion proteins directly to cell culture. NC6 SV40 mouse fibroblasts were plated overnight in 6-well tissue culture plates. The following day, C- or N-terminal FXN-TAT fusion proteins were added directly to cell culture media at a final concentration of 1.0 µM. Cells were treated with protein for four hours, following which they were trypsinized to remove non-incorporated protein and replated. Cells were allowed to adhere overnight. The following day, cells were lysed in standard cell lysis buffer, and whole cell lysates were ran on SDS-PAGE gels for Western Blot analysis. Human FXN was stained using mAb18A5DB1, which does not cross-react with murine FXN. IMR32, a human neuroblastoma line known to express FXN, was used as a positive control. In C-terminal FXN-TAT fusion protein-treated cells, the intermediate and mature form of the FXN molecule is apparent. Taken together, these data suggest that efficient mitochondrial processing of FXN-TAT occurs subsequent to mitochondrial targeting.

Having established that the C terminal FXN-TAT fusion protein can traffic correctly to the mitochondria when directly injected into the cell cytoplasm, we next investigated the ability of the protein to access the mitochondria when delivered exogenously to cells in tissue culture media. Without wishing to be bound by any particular theory, as TAT mediated protein transduction is postulated to occur through vesicular macropinocytosis (Kaplan, et al. *J Control Release*. 2005 Jan. 20; 102(1):247-53), it is contemplated that mitochondrial targeting of FXN-TAT following exogenous protein delivery may involve one or more of the following three steps: transduction of cells; escape from intracellular vesicles; and entry into mitochondria. Consistent with the data from direct cytosolic electroporation of protein, C terminal but not N terminal FXN-TAT was shown to localize to the mitochondria of cells following exogenous addition of protein to cell cultures (FIG. 4). Once again, staining for N terminal FXN-TAT fusion protein was negative. The inability to visualize N terminal FXN-TAT within cells is not due to the molecule's inability to enter cells. When N terminal FXN-TAT fusion protein was exogenously added to cells cultured in the presence of the drug chloroquine, which inhibits vesicular acidification in cells, the protein was visualized throughout the cell cytoplasm (FIG. 5). However, the staining did not localize to mitochondria but rather assumed a vesicular distribution.

Taken together, these data indicate that both N terminal and C terminal FXN-TAT fusion proteins enter cells. Without wishing to be bound by any theories, it is likely that some of the FXN-TAT fusion protein is able to escape macropinosomes, while some remains trapped inside, to be degraded by acid hydrolases and proteases. FXN-TAT fusion protein which escapes macropinosomes can traffic to the mitochondria if the TAT peptide is placed on the C terminus, but becomes degraded in the cytoplasm if the TAT peptide is placed on the N terminus Although the experiments described here use a TAT peptide as mitochondrial penetrating sequence, it is contemplated that the results described herein apply to other mitochondrial penetrating peptides.

Example 3: Processing of C Terminal FXN-TAT Fusion Proteins within Mitochondria

Experiments described in this example demonstrate that recombinant C terminal FXN-TAT fusion protein are processed to mature form within the mitochondrial such that the FXN protein is therapeutically active.

FXN protein is produced as a precursor molecule that is processed to a mature form within the mitochondria (Condo, et al. *Hum Mol Genet*. 2007 Jul. 1; 16(13):1534-40). This process generally occurs in two steps, yielding an intermediate and mature form of the molecule (Schmucker, et al. *Hum Mol Genet*. 2008 Nov. 15; 17(22):3521-31). While the C terminal FXN-TAT protein was shown to localize to the mitochondria when added exogenously to cells, it was not known if the presence of the TAT peptide would affect mitochondrial processing.

In order to determine the maturation state of exogenously delivered FXN, whole cell extracts were prepared from FXN-TAT treated cells and FXN processing was assessed by Western blot.

In this experiment, cell cultures were trypsin treated, washed once in PBS/2.5% BSA and lysed in mitochondrial lysis buffer (Mitosciences, Eugene, Ore) supplemented with 1× protease inhibitor cocktail (HALT protease inhibitor, Pierce/Thermo Scientific, Rockland Ill.). Cell lysates were normalized for protein content by BCA assay (Pierce/Thermo Scientific) and equivalent amounts loaded to 8% Tris-glycine SDS-PAGE gels (Novex/Invitrogen). Following transfer to PVDF membranes and blocking in 5% non-fat milk, blots were stained with anti-human FXN monoclonal antibody 18A5DB1 at 2.5 µg/mL followed by HRP conjugated goat anti-mouse IgG at 1:10,000 (v/v) dilution.

As shown in FIG. 5, C terminal FXN-TAT was processed to the intermediate and mature form in cells. Endogenous human FXN from human neuroblastoma cells is shown as a control (note the slight increase in size of the intermediate and mature form of the molecule due to the presence of TAT peptide). Consistent with the imaging data described in Example 2, N terminal FXN-TAT fusion protein cannot be detected in whole cell lysates of cells treated with exogenous N terminal FXN-TAT fusion protein.

Example 4: C Terminal FXN-TAT Fusion Protein is Capable of Substituting for Native Frataxin Function Experiments described in this example show that recombinant C terminal FXN-TAT fusion protein was active in a cell based screen for FXN function and was capable of substituting for native frataxin function.

Having determined that exogenously delivered C terminal FXN-TAT fusion protein was properly delivered to the mitochondria of cells and processed by mitochondrial processing enzymes to the mature form of the molecule, we next determined whether the protein was active in a cell based screen for FXN function. As described above, NC6 SV40 cells are a murine fibroblast reporter cell line in which one FXN allele is completely deleted and the remaining allele is flanked by lox P sites. Upon addition of the cre recombinase to these cells, genomic FXN is completely eliminated and the cells typically die within 5-9 days. This system was therefore ideal The cre/loxP assay for FXN deletion has been described previously (see e.g., Calmels, et al. *PLoS One*, 2009 Jul. 24; 4(7): e6379). In brief, cells were transformed murine fibroblasts in which one endogenous FXN allele has been knocked out and the other is flanked by loxP recombination sites. Introduction of bacterial cre recombinase (delivered as an eGFP fusion protein) renders the cells FXN null. In most experiments, cre-eGFP plasmid was transfected into subconfluent NC6 SV40 cells using Fugene 6 transfection reagent (Roche, Basel, Switzerland). GFP positive cells were sorted on a FACs ARIA cell sorter (BD Biosciences, Franklin Lakes, N.J.) 24 hours following transfection. Positively transfected cells were treated with C terminal FXN-TAT, as described, 48 hours following cell sort. Cell proliferation was assayed 7 days following protein treatment using the CyQuant NF cell proliferation kit (Molecular Probes/Invitrogen, Carlsbad, Calif.).

In one set of experiments, C terminal FXN-TAT fusion protein was delivered directly to the mitochondria following transfection with a FXN-TAT expression construct. In these experiments, cre recombinase was co-transfected with FXN-TAT eukaryotic expression construct, and double transfected cells were directly sorted into 96 well plates. In another set of experiments, C terminal FXN-TAT fusion protein was exogenously delivered to cells from tissue culture media.

Figure 7:
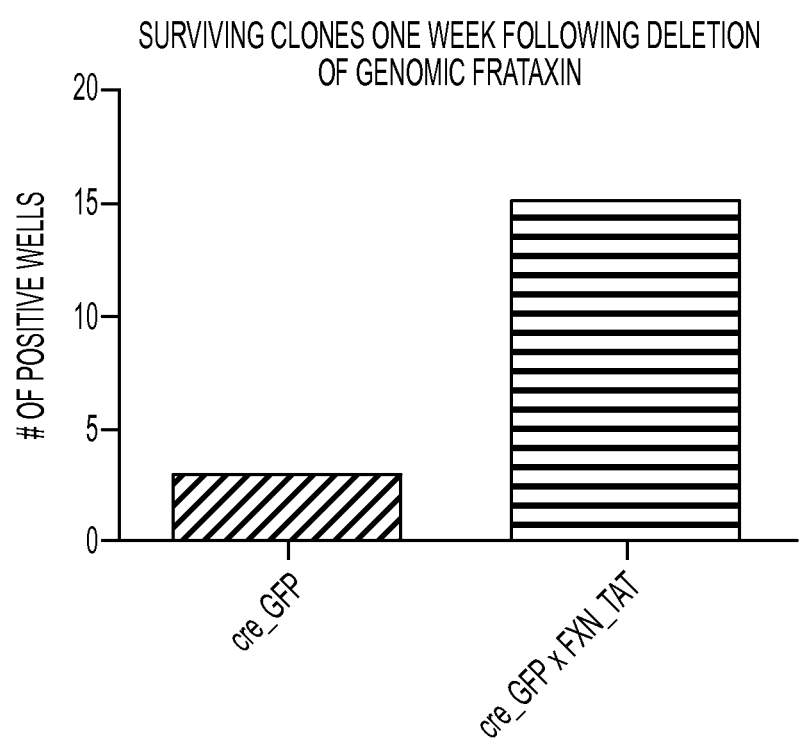
FIG. 7 depicts exemplary cell death rescue experiments in mouse fibroblasts after expression of C-terminal FXN-TAT fusion protein. NC6 SV40 mouse fibroblasts, which are an engineered cell line in which one genomic FXN allele has been deleted and the other is flanked by loxP sites, were co-transfected with cre recombinase (delivered as a cre-GFP fusion) and FXN-TAT expression plasmid. Control cells were transfected with cre recombinase alone. The following day, GFP+ cells were sorted directly into 96-well plates. Plates were cultured for 7 days following the cell sort, at which point wells were fixed in 4% paraformaldehyde and stained with 2 µg/mL Hoechst dye to identify nuclei. Cells with positive clones (greater than 25 cells per well) were manually scored at low power on a widefield epifluorescent microscope. This experiment was repeated twice, with similar results.
Figure 8:
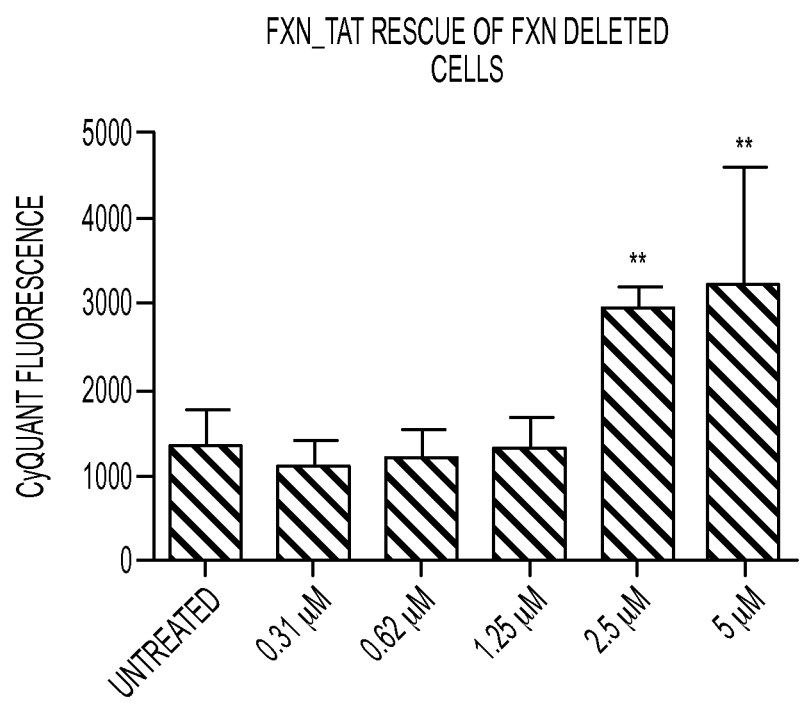
FIG. 8 depicts exemplary cell death rescue experiments in mouse fibroblasts after exogenous addition of C-terminal FXN-TAT fusion protein directly to cell culture. NC6 SV40 fibroblasts were transfected with cre recombinase (delivered as a cre-GFP fusion). The following day, GFP$^+$ cells were sorted into individual wells of a 96-well plate at 1000 cells per well (4 wells per condition). Two days following the cell sort, C-terminal FXN-TAT fusion protein was directly added to the indicated wells at increasing doses, up to 5 µM. Plates were cultured for 7 days following addition of protein. On day 7, cell proliferation was quantified fluorometrically (CyQuant NF cell proliferation assay). This experiment was repeated three times, with similar results.

As shown in FIGS. 7 and 8, C terminal FXN-TAT fusion protein had a protective effect on cells in which germline FXN had been deleted. In the case of C terminal FXN-TAT fusion protein replacement, statistically significant improvement in cell survival was seen at doses equal to or greater than 2.5 µM total protein added. Taken together, these data indicate that C terminal FXN-TAT fusion protein is active within cells and can substitute for native FXN.

The cell based assay used to verify C terminal FXN-TAT fusion protein bioactivity was performed in fibroblasts, a convenient cell type in which to generate a cell based screen. However, we also extended our studies to cells that are physiologically relevant target cells for FRDA, e.g., cells that are particularly sensitive to FXN deficiency during FRDA progression, including neurons from the dorsal root ganglia (DRG) and cardiomyocytes. Primary rat DRG cells were purchased from Lonza (Basel, Switzerland) and cultured according to the manufacturer's specifications. Primary mouse cardiomyocytes (Cor.AT cells) were purchased from Axiogenesis (Cologne, Germany) and cultured according to the manufacturer's specifications. In this experiment, exogenous C terminal FXN-TAT fusion protein was delivered to cells via culture media.

Figure 9:
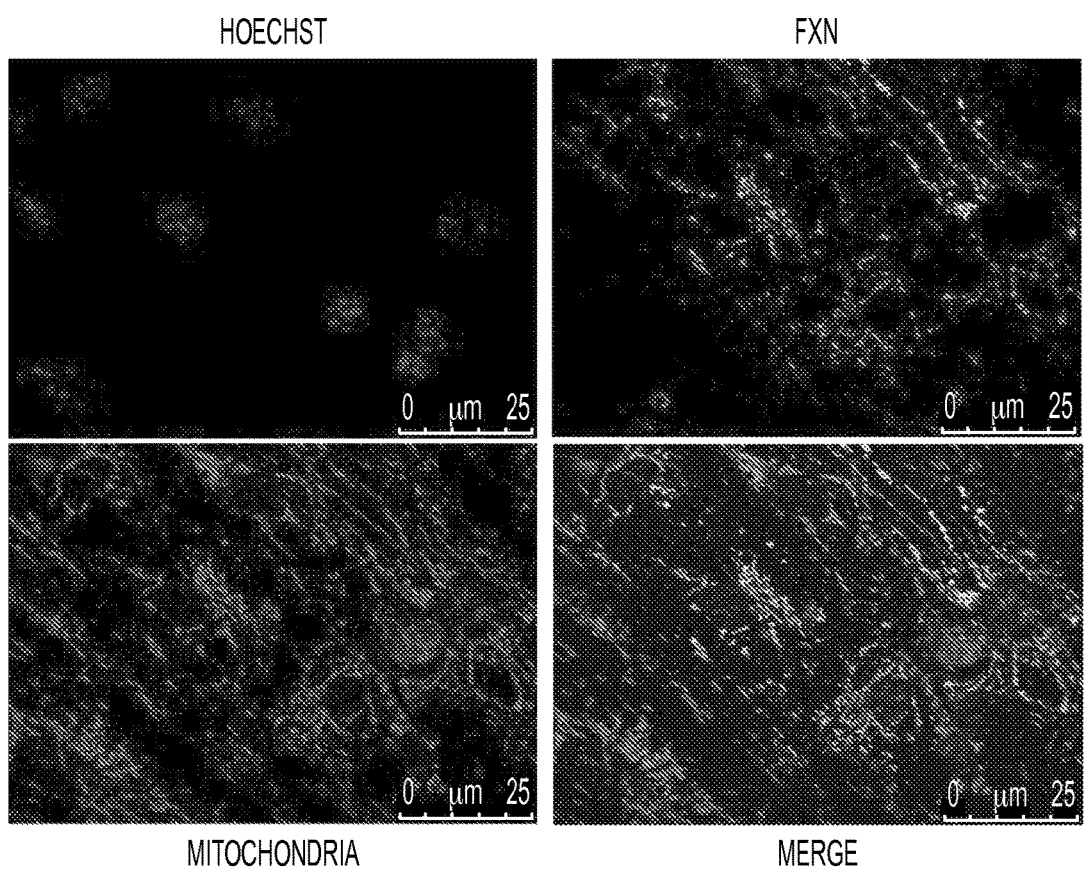
FIG. 9 depicts exemplary results illustrating mitochondrial accumulation of C-terminal FXN-TAT fusion protein in primary murine neuronal cell cultures following exogenous addition of protein directly to cell culture media. Primary murine DRG cell cultures were purchased from a commercial source (Lonza) and cultured as indicated. Five days following addition of mitotic inhibitor to kill proliferating cells, the cultures were primarily neurons. On day 5 post-plating, C-terminal FXN-TAT fusion protein was added directly to culture media at a final concentration of 1.3 µM. The following day, cells were treated with 200 nM Mitotracker Red CMX Rosamine for thirty minutes to stain mitochondria, then fixed and processed for anti-FXN immunofluorescent staining using monoclonal antibody 18A5DB1 (from Mitosciences, specific for human FXN).
Figure 10:
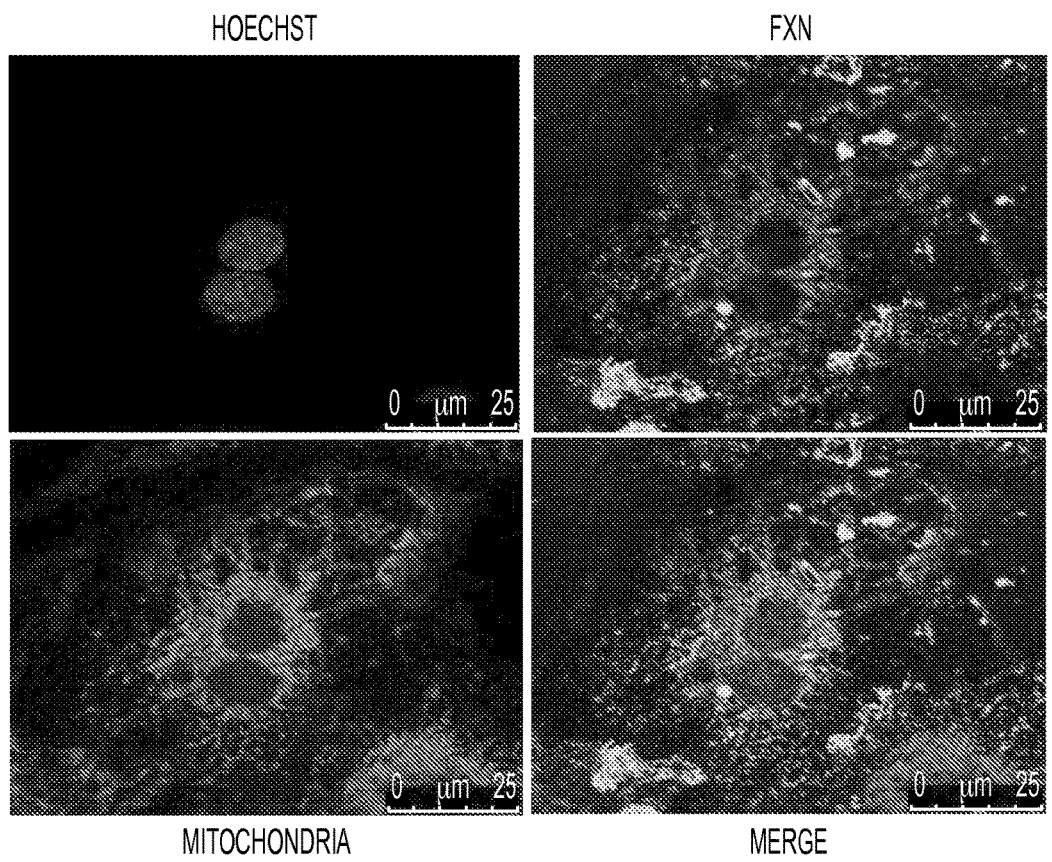
FIG. 10 depicts exemplary results illustrating mitochondrial accumulation of C-terminal FXN-TAT fusion protein in primary murine cardiomyocytes following exogenous addition of protein directly to cell culture media. Primary murine cardiomyocyte cell cultures were purchased from a commercial source (Axiogenesis) and cultured as indicated. Three days following plating, synchronous cell beating could be visualized in the culture, indicating that healthy and functional cardiomyocytes were present. On day 5 post-plating, C-terminal FXN-TAT fusion protein was added directly to culture media at a final concentration of 2.0 µM. The following day, cells were treated with 200 nM Mitotracker Red CMX Rosamine for thirty minutes to stain mitochondria, then fixed and processed for anti-FXN immunofluorescent staining using monoclonal antibody 18A5DB1 (from Mitosciences, specific for human FXN).

As can be seen in FIGS. 9 and 10, complete (in the case of primary DRG neurons) and partial (in the case of primary cardiomyocytes) co-localization of C terminal FXN-TAT and mitochondria was observed in these cultures. Taken together, these data suggest that C terminal FXN-TAT fusion protein is capable of targeting the in vivo cellular targets relevant to FRDA pathology.

Example 5: Treatment of FRDA Using Recombinant C-Terminal FXN-TAT in Disease Model Experiments described in this example are designed to show that recombinant FXN-TAT can be used to effectively treat FRDA disease.

Non-human animal models have been developed to study FRDA. For example, several mouse models for FRDA have been generated, including classical FXN knockout mice, classical FXN knockin mice, and conditional knockout mice. Homozygous deletion of FXN in the classical FXN knockout mouse causes embryonic lethality a few days after implantation (Cossee et al. *Hum Mol Genet* 9:1219 2000). Knockin mice having a $(GAA)_{230}$ repeat within the mouse FXN gene express 25-30% of wild-type FXN levels and do not develop abnormalities of motor coordination, cardiomyopathy, iron metabolism, or response to iron loading up to the age of 1 year (Miranda et al. *FEBS Letters* 512:291 2002). Two conditional knock-out models, based on a Cre-lox system, have been generated in which FXN was deleted specifically in skeletal muscle under a muscle creatine kinase (MCK) promoter or cardiac muscle under a neuron-specific enolase (NSE) promoter (Puccio et al. *Nature Genetics* 27:181 2001). These conditional knockout mice are viable and reproduce important progressive pathophysiological and biochemical features of FRDA in humans, including cardiac hypertrophy, large sensory neuron dysfunction, deficient activities of complexes I-III of the respiratory chain and of the aconitases, and intramitochondrial iron accumulation.

First, in-life evaluations, such as general health, weekly body weights, and performance in locomotor tests such as rotarod, gait analysis and open field test are performed. Mice are administered varying doses of recombinant C-terminal FXN-TAT fusion protein or vehicle control via appropriate delivery methods (e.g., intravenously). Control wild-type mice are untreated. Protein levels and enzyme activity (e.g., assayed by increased enzyme activity in downstream targets such as aconitase and succinate dehydrogenase in affected tissue, such as, for example, heart, brain, and spinal cord) in serum and/or tissue are evaluated. Cardiac and/or neuromuscular function are evaluated. Intramitochondrial iron accumulation is evaluated by appropriate methods (e.g., transmission electron microscopy of tissue sections). Histopathological examination of the heart, brain and spinal cord is performed at autopsy. Exemplary histopathological markers of FA disease include, but are not limited to, fibrosis of the heart, left ventricular hypertrophy, autophagic vesicles in sensory neurons, demyelination of the spinal column, heavy metal accumulation within the brain (dentate nucleus), swollen mitochondria within the heart, brain and spinal column. Animals treated with FXN-TAT display improved cardiac and/or neuromuscular function and/or decreased intramitochondrial iron accumulation and/or decreased histopathological markers of FA disease as compared to vehicle control treated animals.

EQUIVALENTS

Those skilled in the art will recognize, or be able to ascertain using no more than routine experimentation, many equivalents to the specific embodiments of the invention described herein. The scope of the present invention is not intended to be limited to the above Description, but rather is as set forth in the appended claims. The articles "a", "an", and "the" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process. Furthermore, it is to be understood that the invention encompasses variations, combinations, and permutations in which one or more limitations, elements, clauses, descriptive terms, etc., from one or more of the claims is introduced into another claim dependent on the same base claim (or, as relevant, any other claim) unless otherwise indicated or unless it would be evident to one of ordinary skill in the art that a contradiction or inconsistency would arise. Where elements are presented as lists, e.g., in Markush group or similar format, it is to be understood that each subgroup of the elements is also disclosed, and any element(s) can be removed from the group. It should it be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth herein. It should also be understood that any embodiment of the invention, e.g., any embodiment found within the prior art, can be explicitly excluded from the claims, regardless of whether the specific exclusion is recited in the specification.

It should also be understood that, unless clearly indicated to the contrary, in any methods claimed herein that include more than one act, the order of the acts of the method is not necessarily limited to the order in which the acts of the method are recited, but the invention includes embodiments in which the order is so limited. Furthermore, where the claims recite a composition, the invention encompasses methods of using the composition and methods of making the composition. Where the claims recite a composition, it should be understood that the invention encompasses methods of using the composition and methods of making the composition.

INCORPORATION OF REFERENCES

All publications and patent documents cited in this application are incorporated by reference in their entirety to the same extent as if the contents of each individual publication or patent document were incorporated herein.

What is claimed is:

1. A targeted therapeutic comprising:
   a therapeutic moiety, which is a polypeptide having an N-terminus and a C-terminus and having an amino acid sequence at least 95% identical to mature human Frataxin protein (SEQ ID NO: 1);
   a mitochondrial targeting peptide sequence fused at the N-terminus of the therapeutic moiety; and
   a mitochondrial membrane-penetrating peptide sequence fused at the C-terminus of the therapeutic moiety,
   wherein the therapeutic moiety is targeted to mitochondria upon cellular entry.

2. The targeted therapeutic of claim 1, wherein the mitochondrial targeting peptide sequence and the mitochondrial membrane-penetrating peptide sequence are fused to the therapeutic moiety in a fusion protein configuration.

3. The targeted therapeutic of claim 1, wherein the mitochondrial targeting peptide sequence has an amino acid sequence at least 95% identical to SEQ ID NO: 2.

4. The targeted therapeutic of claim 1, wherein the mitochondrial membrane-penetrating peptide has an amino acid sequence at least 95% identical to HIV-TAT peptide GYGRKKRRQRRR (SEQ ID NO: 5).

* * * * *

SEQUENCE LISTING

<160> NUMBER OF SEQ ID NOS: 7

<210> SEQ ID NO 1
<211> LENGTH: 130
<212> TYPE: PRT
<213> ORGANISM: Homo sapiens

<400> SEQUENCE: 1

```
Ser Gly Thr Leu Gly His Pro Gly Ser Leu Asp Glu Thr Thr Tyr Glu
1               5                   10                  15

Arg Leu Ala Glu Glu Thr Leu Asp Ser Leu Ala Glu Phe Phe Glu Asp
            20                  25                  30

Leu Ala Asp Lys Pro Tyr Thr Phe Glu Asp Tyr Asp Val Ser Phe Gly
        35                  40                  45

Ser Gly Val Leu Thr Val Lys Leu Gly Gly Asp Leu Gly Thr Tyr Val
    50                  55                  60

Ile Asn Lys Gln Thr Pro Asn Lys Gln Ile Trp Leu Ser Ser Pro Ser
65                  70                  75                  80

Ser Gly Pro Lys Arg Tyr Asp Trp Thr Gly Lys Asn Trp Val Tyr Ser
                85                  90                  95

His Asp Gly Val Ser Leu His Glu Leu Leu Ala Ala Glu Leu Thr Lys
            100                 105                 110

Ala Leu Lys Thr Lys Leu Asp Leu Ser Ser Leu Ala Tyr Ser Gly Lys
        115                 120                 125

Asp Ala
    130
```

<210> SEQ ID NO 2
<211> LENGTH: 20
<212> TYPE: PRT
<213> ORGANISM: Homo sapiens

<400> SEQUENCE: 2

Met Trp Thr Leu Gly Arg Arg Ala Val Ala Gly Leu Leu Ala Ser Pro
1               5                   10                  15

Ser Pro Ala Gln
            20

<210> SEQ ID NO 3
<211> LENGTH: 80
<212> TYPE: PRT
<213> ORGANISM: Homo sapiens

<400> SEQUENCE: 3

Met Trp Thr Leu Gly Arg Arg Ala Val Ala Gly Leu Leu Ala Ser Pro
1               5                   10                  15

Ser Pro Ala Gln Ala Gln Thr Leu Thr Arg Val Pro Arg Pro Ala Glu
            20                  25                  30

Leu Ala Pro Leu Cys Gly Arg Arg Gly Leu Arg Thr Asp Ile Asp Ala
            35                  40                  45

Thr Cys Thr Pro Arg Arg Ala Ser Ser Asn Gln Arg Gly Leu Asn Gln
50                  55                  60

Ile Trp Asn Val Lys Lys Gln Ser Val Tyr Leu Met Asn Leu Arg Lys
65                  70                  75                  80

<210> SEQ ID NO 4
<211> LENGTH: 210
<212> TYPE: PRT
<213> ORGANISM: Homo sapiens

<400> SEQUENCE: 4

Met Trp Thr Leu Gly Arg Arg Ala Val Ala Gly Leu Leu Ala Ser Pro
1               5                   10                  15

Ser Pro Ala Gln Ala Gln Thr Leu Thr Arg Val Pro Arg Pro Ala Glu
            20                  25                  30

Leu Ala Pro Leu Cys Gly Arg Arg Gly Leu Arg Thr Asp Ile Asp Ala
            35                  40                  45

Thr Cys Thr Pro Arg Arg Ala Ser Ser Asn Gln Arg Gly Leu Asn Gln
50                  55                  60

Ile Trp Asn Val Lys Lys Gln Ser Val Tyr Leu Met Asn Leu Arg Lys
65                  70                  75                  80

Ser Gly Thr Leu Gly His Pro Gly Ser Leu Asp Glu Thr Thr Tyr Glu
            85                  90                  95

Arg Leu Ala Glu Glu Thr Leu Asp Ser Leu Ala Glu Phe Phe Glu Asp
            100                 105                 110

Leu Ala Asp Lys Pro Tyr Thr Phe Glu Asp Tyr Asp Val Ser Phe Gly
            115                 120                 125

Ser Gly Val Leu Thr Val Lys Leu Gly Gly Asp Leu Gly Thr Tyr Val
            130                 135                 140

Ile Asn Lys Gln Thr Pro Asn Lys Gln Ile Trp Leu Ser Ser Pro Ser
145                 150                 155                 160

Ser Gly Pro Lys Arg Tyr Asp Trp Thr Gly Lys Asn Trp Val Tyr Ser
                165                 170                 175

```
His Asp Gly Val Ser Leu His Glu Leu Leu Ala Ala Glu Leu Thr Lys
            180                 185                 190

Ala Leu Lys Thr Lys Leu Asp Leu Ser Ser Leu Ala Tyr Ser Gly Lys
        195                 200                 205

Asp Ala
    210

<210> SEQ ID NO 5
<211> LENGTH: 12
<212> TYPE: PRT
<213> ORGANISM: Human immunodeficiency virus

<400> SEQUENCE: 5

Gly Tyr Gly Arg Lys Lys Arg Arg Gln Arg Arg Arg
1               5                   10

<210> SEQ ID NO 6
<211> LENGTH: 222
<212> TYPE: PRT
<213> ORGANISM: Artificial Sequence
<220> FEATURE:
<223> OTHER INFORMATION: C-terminal FXN-TAT fusion protein

<400> SEQUENCE: 6

Met Trp Thr Leu Gly Arg Arg Ala Val Ala Gly Leu Leu Ala Ser Pro
1               5                   10                  15

Ser Pro Ala Gln Ala Gln Thr Leu Thr Arg Val Pro Arg Pro Ala Glu
            20                  25                  30

Leu Ala Pro Leu Cys Gly Arg Arg Gly Leu Arg Thr Asp Ile Asp Ala
        35                  40                  45

Thr Cys Thr Pro Arg Arg Ala Ser Ser Asn Gln Arg Gly Leu Asn Gln
    50                  55                  60

Ile Trp Asn Val Lys Lys Gln Ser Val Tyr Leu Met Asn Leu Arg Lys
65                  70                  75                  80

Ser Gly Thr Leu Gly His Pro Gly Ser Leu Asp Glu Thr Thr Tyr Glu
                85                  90                  95

Arg Leu Ala Glu Glu Thr Leu Asp Ser Leu Ala Glu Phe Phe Glu Asp
            100                 105                 110

Leu Ala Asp Lys Pro Tyr Thr Phe Glu Asp Tyr Asp Val Ser Phe Gly
        115                 120                 125

Ser Gly Val Leu Thr Val Lys Leu Gly Gly Asp Leu Gly Thr Tyr Val
    130                 135                 140

Ile Asn Lys Gln Thr Pro Asn Lys Gln Ile Trp Leu Ser Ser Pro Ser
145                 150                 155                 160

Ser Gly Pro Lys Arg Tyr Asp Trp Thr Gly Lys Asn Trp Val Tyr Ser
                165                 170                 175

His Asp Gly Val Ser Leu His Glu Leu Leu Ala Ala Glu Leu Thr Lys
            180                 185                 190

Ala Leu Lys Thr Lys Leu Asp Leu Ser Ser Leu Ala Tyr Ser Gly Lys
        195                 200                 205

Asp Ala Gly Tyr Gly Arg Lys Lys Arg Arg Gln Arg Arg
    210                 215                 220

<210> SEQ ID NO 7
<211> LENGTH: 222
<212> TYPE: PRT
<213> ORGANISM: Artificial Sequence
<220> FEATURE:
<223> OTHER INFORMATION: N-terminal FXN-TAT fusion protein
```

```
<400> SEQUENCE: 7

Gly Tyr Gly Arg Lys Lys Arg Arg Gln Arg Arg Met Trp Thr Leu
1               5                   10                  15

Gly Arg Arg Ala Val Ala Gly Leu Leu Ala Ser Pro Ser Pro Ala Gln
            20                  25              30

Ala Gln Thr Leu Thr Arg Val Pro Arg Pro Ala Glu Leu Ala Pro Leu
        35              40                  45

Cys Gly Arg Arg Gly Leu Arg Thr Asp Ile Asp Ala Thr Cys Thr Pro
50                      55                  60

Arg Arg Ala Ser Ser Asn Gln Arg Gly Leu Asn Gln Ile Trp Asn Val
65                  70                  75                  80

Lys Lys Gln Ser Val Tyr Leu Met Asn Leu Arg Lys Ser Gly Thr Leu
                85              90                  95

Gly His Pro Gly Ser Leu Asp Glu Thr Thr Tyr Glu Arg Leu Ala Glu
            100                 105                 110

Glu Thr Leu Asp Ser Leu Ala Glu Phe Phe Glu Asp Leu Ala Asp Lys
        115                 120                 125

Pro Tyr Thr Phe Glu Asp Tyr Asp Val Ser Phe Gly Ser Gly Val Leu
    130                 135                 140

Thr Val Lys Leu Gly Gly Asp Leu Gly Thr Tyr Val Ile Asn Lys Gln
145                 150                 155                 160

Thr Pro Asn Lys Gln Ile Trp Leu Ser Ser Pro Ser Ser Gly Pro Lys
                165                 170                 175

Arg Tyr Asp Trp Thr Gly Lys Asn Trp Val Tyr Ser His Asp Gly Val
            180                 185                 190

Ser Leu His Glu Leu Leu Ala Ala Glu Leu Thr Lys Ala Leu Lys Thr
        195                 200                 205

Lys Leu Asp Leu Ser Ser Leu Ala Tyr Ser Gly Lys Asp Ala
    210                 215                 220
```